United States Patent
Giuliani et al.

(10) Patent No.: US 8,546,147 B2
(45) Date of Patent: Oct. 1, 2013

(54) IMIDAZO[1,2-α]PYRAZIN-3(7H)-ONE DERIVATIVES BEARING A NEW ELECTRON-RICH STRUCTURE

(75) Inventors: Germano Giuliani, Siena (IT); Andrea Cappelli, Siena (IT); Maurizio Anzini, Siena (IT); Salvatore Vomero, Siena (IT)

(73) Assignee: Universita degli Studi di Siena, Siena (IT)

( * ) Notice: Subject to any disclaimer, the term of this patent is extended or adjusted under 35 U.S.C. 154(b) by 0 days.

(21) Appl. No.: 13/383,447

(22) PCT Filed: Jul. 12, 2010

(86) PCT No.: PCT/IB2010/053187
§ 371 (c)(1),
(2), (4) Date: Mar. 20, 2012

(87) PCT Pub. No.: WO2011/007314
PCT Pub. Date: Jan. 20, 2011

(65) Prior Publication Data
US 2012/0171703 A1    Jul. 5, 2012

Related U.S. Application Data

(60) Provisional application No. 61/224,953, filed on Jul. 13, 2009.

(51) Int. Cl.
G01N 21/76 (2006.01)
C12Q 1/66 (2006.01)
C07D 235/02 (2006.01)

(52) U.S. Cl.
USPC ............ 436/172; 435/7.72; 435/8; 548/303.1

(58) Field of Classification Search
None
See application file for complete search history.

(56) References Cited

FOREIGN PATENT DOCUMENTS

| | | |
|---|---|---|
| GB | 2 425 535 A | 11/2006 |
| JP | 2010/090319 A1 | 8/2010 |
| WO | 2004/072299 A1 | 8/2004 |
| WO | 2008/118445 A1 | 10/2008 |

OTHER PUBLICATIONS

Gonzelez, Victor. Synthesis, luminescence, and applications of coelenterazine and its analogs. Feb. 26, 2007, pp. 17-24.*
Wu, C., et al: "Chemi- and bioluminescence of coelenterazine analogues with a conjugated group at the C-8 position", Tetrahedron Letters, Elsevier, Amsterdam, NL LNKDDOI: 10.1016/S0040-4039(01)00340-9, vol. 42, No. 16, Apr. 16, 2001, pp. 2997-3000, ISSN: 0040-4039.
Isobe, M., et al: "Chemistru of photoproteins as interface between bioactive molecules and protein function", Pure & Applied Chemistry, Pergamon Press, Oxford, GB, vol. 70, No. 11, Jan. 1, 1998, pp. 2085-2092, ISSN: 0033-4545.
Teranishi, K., et al: "Synthesis and chemiluminescence of coelenterazine (Qplophorus luciferin) analogues", Bulletin of the Chemical Society of Japan, Chemical Society of Japan, Tokyo, JP, vol. 63, No. 11, Nov. 1, 1990, pp. 3132-3140, ISSN: 0009-2673.
Bondar Vladimir, S., et al: "Cadmium-induced luminescence of recombinant photoprotein obelin", 1995, Biochimica et Biophysica Acta, vol. 1231, NR. 1, pp. 29-32 , ISSN: 0006-3002.

* cited by examiner

*Primary Examiner* — Shafiqul Haq
(74) *Attorney, Agent, or Firm* — Lucas & Mercanti, LLP

(57) ABSTRACT

The present invention relates to compound of formula I: and their use as chemiluminescent and/or bioluminescent reagents.

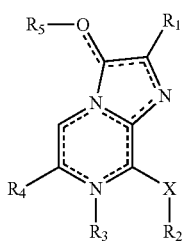

13 Claims, 8 Drawing Sheets

Coelenterazine (1)  
$\lambda em = 470$ nm

Benzothiazoline (2)  
$\lambda em = 565$ nm

Enol Formate (3)  
$\lambda em = 536$ nm

Imidazopyrazinone (4)  
$\lambda em = 465$ nm

IMIDAZO[1,2-α]PYRAZIN-3(7H)-ONE DERIVATIVES BEARING A NEW ELECTRON-RICH STRUCTURE

CROSS-REFERENCE TO RELATED APPLICATIONS

This application is a 371 of PCT/IB2010/053187, filed Jul. 12, 2010, which claims the benefit of U.S. Provisional Patent Application No. 61/224,953, filed Jul. 13, 2009, the contents of each of which are incorporated herein by reference.

FIELD OF THE INVENTION

The present invention relates to imidazo[1,2-a]pyrazin-3 (7H)-one derivatives comprising an hetero-atom and their use as chemiluminescent and/or bioluminescent reagents.

BACKGROUND OF THE INVENTION

Genetic reporter systems have contributed greatly to the study of eukaryotic gene expression and regulation. Although reporter genes have played a significant role in numerous applications, both in vitro and in vivo, they are most frequently used as indicators of transcriptional activity in cells.[1]

Typically, a reporter gene is joined to a promoter sequence in an expression vector that is transferred into cells. Following transfer, the cells are assayed for the presence of the reporter by directly measuring the reporter protein itself or the enzymatic activity of the reporter protein. An ideal reporter gene is one that is not endogenously expressed in the cell of interest and it is amenable to assays that are sensitive, quantitative, rapid, easy, reproducible and safe.

Fundamentally, an assay is a means for translating a biomolecular effect into an observable parameter. While there are theoretically many strategies by which this can be achieved, in practice the reporter assays capable of delivering the speed, accuracy and sensitivity necessary for effective screening are based on photon production.

Photon production is realized primarily through fluorescence and chemiluminescence. Both processes yield photons as a consequence of energy transitions from excited-state molecular orbitals to lower energy orbitals. However, they differ in how the excited-state orbitals are created. In chemiluminescence, the excited states are the product of exothermic chemical reactions, whereas in fluorescence the excited states are created by absorption of light.

Assays based on fluorescence or chemiluminescence can yield high sample throughput. The introduction of the Fluorometric Imaging Plate Reader (FLIPR™, Molecular Devices),[2] an image-based instrument capable of measuring 384 wells simultaneously, has allowed extensive use of fluorescent dye-based $Ca^{2+}$ mobilization assays in the high throughput screening (HTS) process.

New capabilities in chemiluminescence, particularly in bioluminescence (when a chemiluminescent reaction occurs in an organism with the aid of an enzyme), are now adding new bioluminescence techniques to HTS.[3]

Bioluminescence is the generation of light by a biochemical reaction involving oxidation of a chemiluminescent substrate (luciferin) via an enzyme (luciferase). Bioluminescence differs from species to species, but the general mechanism begins with the oxidation of a luciferin by its luciferase enzyme in the presence of $O_2$ to form an excited state of the oxidation product (oxyluciferin).[4]

Bioluminescence colors can range from blue to red (FIG. 1). The particular wavelength that is emitted depends in part on the type of luciferins employed, and these cover diverse structural classes (FIG. 1, structure 1-4).[5] Luciferases from organisms that yield very bright bioluminescence have been adapted for the use as reporters in HTS assays, the most common being from the jellyfish Aequorea Victoria (Aequorin), the sea pansy Renilla reniformis (RLuc), and the firefly Photinus pyralis. Because RLuc uses the same substrate (coelenterazine, 1) as Aequorin, it yields the same products, emits a photon with similar spectral characteristics and the reaction mechanisms are expected to be similar.[6] But Aequorin can also function as a calcium dependent luciferase (RLuc itself is not calcium dependent).

This phenomenon has been extensively used in different formats for life science research and drug discovery owing to its extremely high sensitivity, replacing advantageously hazardous methods using, for instance, radioelement.

There are five main problem with radioisotopes,[1] placing some practical limitations on their application in the biological laboratory:

1) Preparation of the isotope; this requires a special, costly apparatus such as a nuclear reactor or particle accelerator together with the safety facilities for handling highly radioactive compounds.
2) Hazard; radioactive isotopes are dangerous, not only at the high levels involved in their preparation but also even at the levels in reagents used in research and clinical laboratories. Safety precautions, including special "hot" rooms and cabinets, together with personnel screening are therefore essential. Special facilities are also required for disposal of radioactive waste.
3) Sensitivity and detection speed; the detection limit for a radioisotope can be estimated from the half-time ($t_{1/2}$) of its decay. The shorter the half life the lower the detection limit: $A_t = A_0\, e^{-kt}$ $k=0.693/t_{1/2}$
  where:
    $A_t$=Amount of pure isotope at time t
    $A_0$=Amount of pure isotope at time 0
    k=decay rate constant=$0.693/t_{1/2}$
4) The consequences of isotope decay; The most sensitively detectable isotopes by their nature decay rapidly. Some decay is so fast as to make the isotopes practically useless. A further problem is the effect of decay on the molecule to which the isotope is attached. Biological molecules, such as proteins, are particularly susceptible to radiolytic damage.
5) The need for a separation step; virtually all analytical applications of radioisotopes require a separation step in order to isolate the appropriate material for radioactive counting. These separation steps introduce imprecision, are sometimes laborious, and complicate automation for clinical application.

Chemiluminescent labels are groups of synthetic organic compounds (e.g. luminol, acridinium esters), cofactors in bioluminescent reactions (ATP, NAD), enzymes (peroxidase, oxidase, kinases, luciferases), and represent a real alternative to a radioimmunoassay and to develop new approaches to advance our knowledge of how cells work.[1]

A large number of luminescent labels can be readily detected within a few second in the fmol-amol range ($10^{-15}$-$10^{-18}$).[1] The improvement of peroxydase "enhancers", the use of luciferins with a higher quantum yield and lower chemical "noise" than luminol,[1] and the use of better peroxidase (e.g. luciferase peroxydase), may enable tipomol ($10^{-21}$) sensitivity to be achieved.

Image intensifiers are available for detecting chemiluminescence as sensitively as a photomultiplier tube,[7] beyond the intensity per unit area necessary to produce an image in the naked eye. Chemiluminescent labels are therefore applicable to light microscopy. A label producing a continuous glow, e.g. peroxydase or luciferase, may be more convenient than one producing a flash.

Several types of homogeneous assay, not requiring a separation step, have been established using chemiluminescent labels. The labelled reagents have been found to have a shelf life of many years. Many clinically useful assay have been established which satisfy the normal criteria for a good immunoassay.[1] The working range can be established by evaluation of the precision profile and good correlation (r>0.95) with its checked radioactive counterpart. The chemiluminescent labels are safe to handle and, unlike radioisotopes, no special precautions appear necessary. Many luciferins are now commercially available and they're relatively easy to synthesise in gram quantities.

Historically,[1] changes in intracellular $Ca^{2+}$ levels have been readily detected using fluorescent dyes that emit light in proportion to the changes in intracellular $Ca^{2+}$ concentration. An alternative approach to indirectly measure changes in $Ca^{2+}$ concentrations involves the use of recombinantly expressed biosensor photoproteins, of which Aequorin is a prototypic example (see Table 1).[8]

Aequorin, has been validated for functional assays of many GPCRs, and the results obtained are comparable to those obtained with the use of fluorescent dyes. However, the adaptation of Aequorin assays to HTS is not always easy due to the low quantum yield of aequorin and the fast kinetics of the reaction.

Coelenterazines are small and hydrophobic molecules that readily cross cell membranes, thereby permitting analysis of intact cell. The donor emission spectrum dependent upon the coelenterazine used, in addiction to the donor protein itself.

The luminescence reaction catalyzed by *Renilla luciferase* (RLuc) is shown in Scheme 1. RLuc catalyzes the enzymatic degradation of coelenterazine, leaving the resultant product, coelenteramide 5, with an electron in an excited state.[10]

Scheme 1: Chemiluminescent mechanism of coelenterazine.

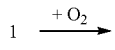

TABLE 1

| Properties | $Ca^{2+}$-sensitive dyes[a] | Photoproteins[b] | GFP sensors[c] |
|---|---|---|---|
| Energy emission | Fluorescence | Chemiluminescence | Fluorescence |
| Detection device | FLIPR | FLIPR, CCD | Microscopy |
| Backgrouns $Ca^{2+}$ | Moderate to high | Low | Moderate/high |
| Signal-to-noise ratio | Low to moderate | High | Moderate |
| Dynamic range of $Ca^{2+}$ change | Low to moderate | High | High |
| Sensitivity | Low to moderate | High | High |
| Adaptability to assay conditions | Low | Moderate/high | Low |
| Cells per well needed | Thousands | Hundreds | Single/hundreds |
| Ease of use in HTS | High | High | Moderate |
| Compound interference | Moderate | None | Moderate |
| Useful for orphan GPCRs | Not easy | Yes | Moderate |
| Targeted to subcellular sites | No | Yes | Yes |
| $Ca^{2+}$ in microdomains | No | Yes | Yes |
| Reaction kinetics | Fast | Photina slow | Fast |
| Used in vivo | No | Yes but rarely | Yes |

Comparison of $Ca^{2+}$-sensitive dyes and photoproteins for HTS.

The bivalent ion $Ca^{2+}$ is a critical second messenger involved in many physiological and signal transduction processes within a cell.[9] The central role of $Ca^{2+}$ in intracellular signalling, and its physical/chemical properties also makes it an attractive reporting molecule for drug discovery (for example, GPCRs, ion channels, and ion exchangers are among the most interesting target classes for the pharmaceutical industry).[8] The use of photoproteins as indicators of $Ca^{2+}$ activation in HTS offers many advantages: low background levels result in a large signal to noise ratio, $Ca^{2+}$ concentrations can be measured at specific cellular sites, tested compounds only require short incubation periods, and reaction kinetics can be followed.

(2) Coelenterazine dioxethanone

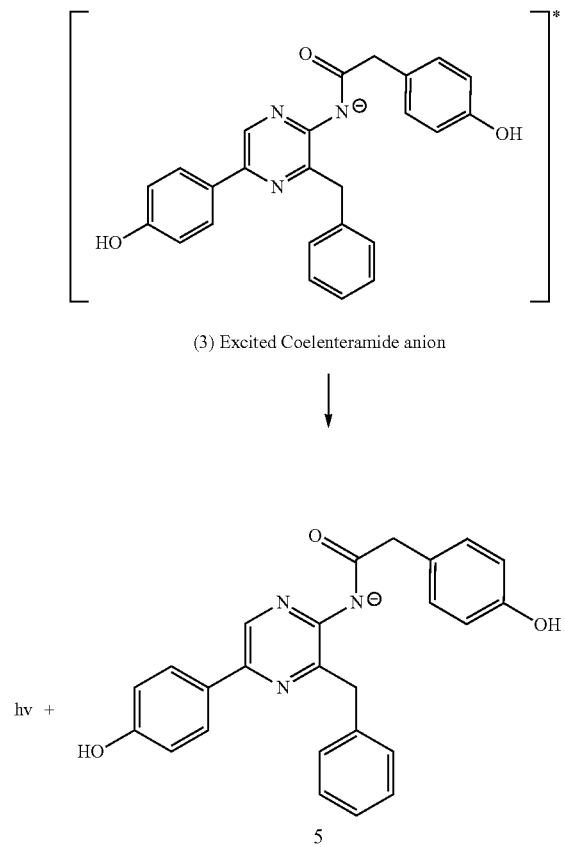

(3) Excited Coelenteramide anion

↓ hv +  [structure 5]

It has been suggested that the blue light emission (λ=481 nm peak for RLuc) associated with coelenterazine bioluminescence is due to the excited state coelenteramide existing in its amide anion form when it is in the protein's enzymatic pocket.[11]

However, at least in the case of photoproteins that use coelenterazine such as Obelin, Aequorin, more recent literature has favored assigning the phenolate anion as the blue emitting species in bioluminescence.[12]

Since the 1970s, a large number of coelenterazine analogs were synthesized to obtain new molecules with improved properties.[13,10] In particular, red shifted emission peak, high quantum yield and better sensibility of $Ca^{2-}$ ions are still needed.

Examples of bioluminescence applications that use the Apoaequorin/Coelenterazine system, include: reporter assays, measuring $Ca^{2-}$ in cells, reactive oxygen species (ROS) detection, protein interaction studies.

Concerning reporter assays, aequorin has been largely used to tag (by plasmid or other engineering methods), recombinant proteins, and then monitor their expression (localization, regulation . . . ).[14] For imaging bioluminescent reporters[15] in intact animals it is highly advantageous for the luciferase to emit a large percentage of its photons in red to near-infrared wavelengths (600-900 nm), as tissue attenuation of optical wavelength photons is minimized in this region of the spectrum[1]. The luciferases that use coelenterazine as their substrate (for example, RLuc, Gaussia princeps luciferase) have served as useful adjuncts to the beetle luciferases in both cell culture and animal experiments.[16] They also have been used in situations where the ATP-dependence and poor thermal stability of the beetle luciferases would be a liability, such as in bioluminescently tagged imaging probes[17] and self-illuminating quantum dots.[18]

However these luciferases have a major limitation for most small-animal imaging applications in that their spectral peaks are in the blue region of the visible spectrum (RLuc, λ=481 nm). From locations deeper than subcutaneous depths, most of the photons that make it out of the animal being imaged are few red-shifted wavelength photons.[19]

However, the use of native coelenterazine in small animal imaging has been hampered by its λ=481 nm peaked emission spectrum as blue wavelengths, that are strongly attenuated in biological tissues.

To overcome this difficulty, research is focused on red-shifting RLuc through a combination of semirational and random mutagenesis, yielding variants with bathochromic shifts of up to 66 nm. Analysis of the most promising variant demonstrated that it was 6-fold brighter than RLuc, and its green emission spectrum (λ=535 nm peak) generated a further 3-fold improvement in photon transport at depths of 1-2 mm of animal tissue.[19]

The interaction between the luciferase and coelenterazine is not well understood, a conclusive answer cannot be given at this time, but it may be that the pyrazine anion of coelenteramide represents a limit to the bathochromic shift that this luciferin-luciferase system can accomplish. Further, redshifts will most likely involve altering the structure of the luciferin, as shown with coelenterazine-v.[10] This particular analog, however, suffers from issues of stability that limits its applicability. Thus, the development of alternative red-shifted coelenterazine analogs more appropriate for small-animal imaging are needed. Another negative aspect of the blue emission of coelenterazine analogs has to be considered. Indeed, due to the high energy of their luminescent intermediates, these molecules show a flash emission which makes the applicability to energy transfer assays difficult.

Consequently, a very fast kinetic of the bioluminescent reaction (few seconds) is observed. The problem is particularly evident in BRET (Bioluminescence Resonance Energy Transfer) where the real time monitoring of biological events needs luminescent substrate with prolonged decay kinetics.[20] To avoid this difficulty, recently modified analogs EnduRen™, ViviRen™ (Promega) were synthesized. EnduRen™ and ViviRen™ (in vivo Renilla Luciferase substrate) are a uniquely engineered coelenterazine-based compounds with protected oxidation sites (see Scheme 2).

Scheme 2.

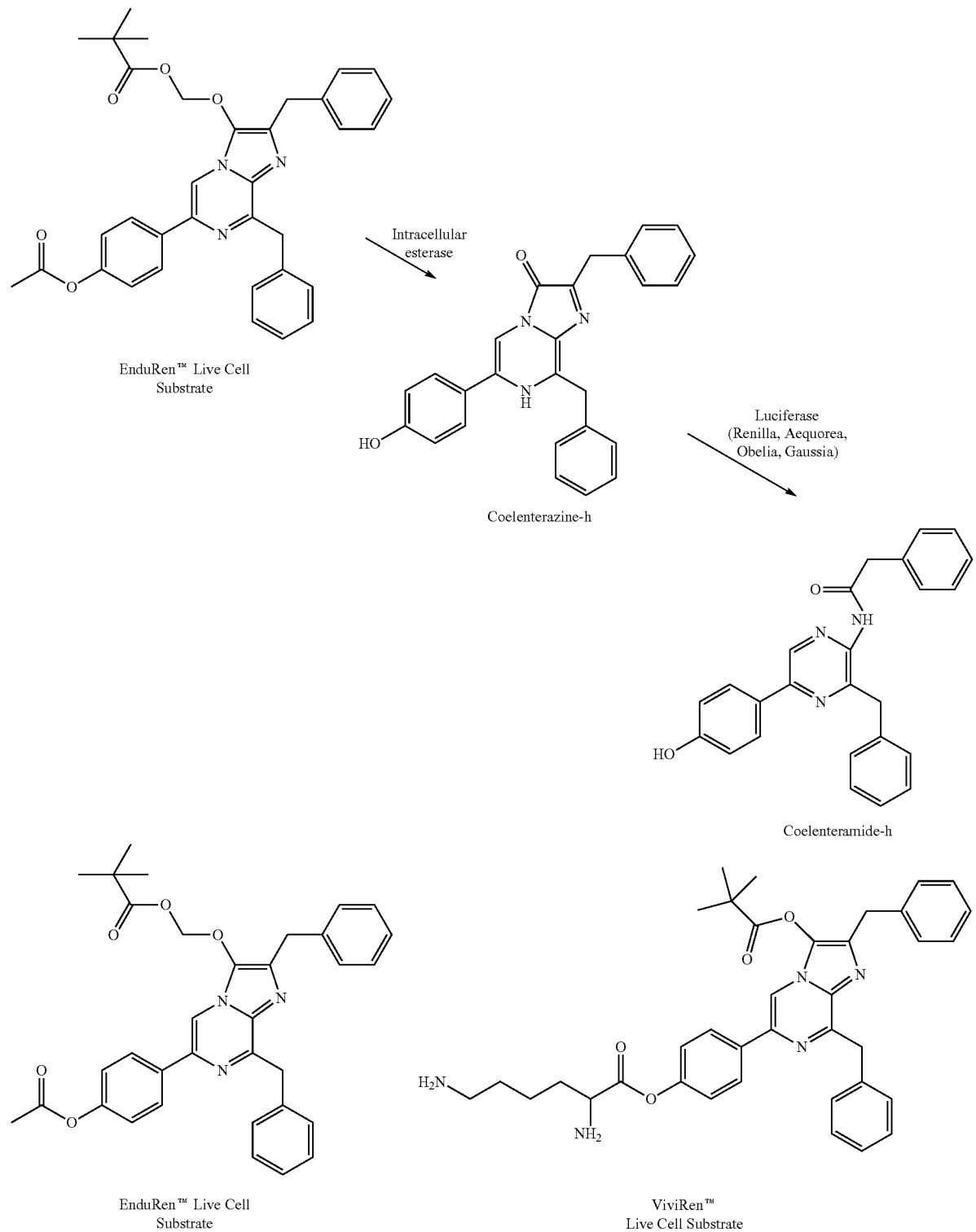

These modifications are designed to minimize substrate degradation and autoluminescence. It is reported that these substrates may have a longer kinetic output when compared to the native coelenterazine substrates when used in an in viva imaging application in a mouse model. Once inside the cell, the protective groups of the substrate are cleaved by intracellular esterases, generating coelenterazine which reacts with RLuc to produce light. Peak luminescence of EnduRen™ is achieved after 1.5 hours of substrate addition to cells, and signal is stable for >24 hours. Peak luminescence of ViviRen™ is achieved after 2 minutes of substrate addition to cells, with signal half-life from 8-15 minutes.

While a wide number of variants of luciferase, obtained through a combination of semi-rational and random mutagenesis, show bathochromic (red-shifted) shifts, the finding of new coelenterazine analogs with improved properties is lacking.

e-Coelenterazine seems to be the more interesting molecule with a red-shifted signal ($\lambda$=510 nm maximum peak of bioluminescence), good quantum yield and high sensibility to $Ca^{2+}$ concentrations. But this molecule presents difficulties for its synthesis and poor stability.[13a]

Literature reports a large number of analogs of the native coelenterazine,[13] with a red-shift of the emission peak of chemiluminescence reaction. Among compounds that have shown the best chemiluminescent properties, many of them bear structural modifications which do not allow the correct fitting of the molecules in the enzymatic binding pocket, and, as expected, no bioluminescence signal was detected. Another problem with the modifications proposed was the reduced lipophilicity of molecules and consequent poor cellular membranes crossing. These compounds were synthesized to better understand the structural properties of the molecules related to the chemiluminescent mechanism. The experiments performed show interesting results;[11] for example, chemiluminescence efficiency, or quantum yield, is lower than bioluminescence's one. The disparity between the chemiluminescent and bioluminescent efficiencies of coelenterazine is attributed to both the conformational stability of the emitter in the protein and the hydrophobic environment surrounding the coelenteramide anion. To test the conformational stability effects on the chemiluminescence of coelenterazine, analogs with rigidifying bridges were synthesized (6-10; Table 2).[13e]

TABLE 2

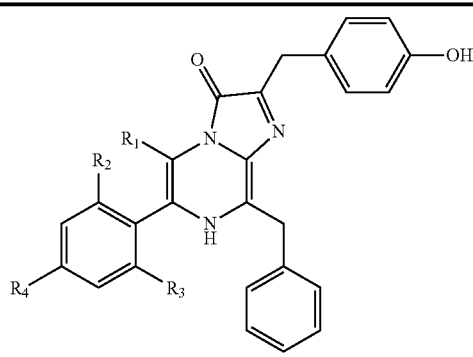

| Compounds | $R_1$ | $R_2$ | $R_3$ | $R_4$ | $\Phi_{Cl}$ (Relative Light Yield) |
|---|---|---|---|---|---|
| 1 | H | H | H | OH | 0.21% (1.0) |
| 6 | —$CH_2$— | | H | OH | 0.31% (1.5) |
| 7 | —$CH_2CH_2$— | | H | OH | 0.48% (2.3) |
| 8 | —$(CH_2)_3$— | | H | OH | 0.31% (1.5) |
| 9 | —$CH_2CH_2OH$ | H | H | OH | 0.10% (0.46) |
| 10 | —$CH_2CH_2$— | | OH | OH | 0% (0.01) |

Chemiluminescence experiments using compounds with a rigid p-hydroxyphenyl group showed increased $\Phi_{Cl}$, with the six-membered ring derivative 7 having the highest quantum yield.

Intramolecular hydrogen bonding effects between the hydroxyl and nitrogen atoms on the imidazopyrazine core decreased the chemiluminescent efficiencies (9,10), supporting the notion that the bioluminescence reaction takes place in a hydrophobic environment in the luciferase enzyme.[13e] Coelenterazine analogs have also been modified to produce bimodal chemiluminescent systems. Typically, imidazopyrazinones can emit blue to yellow light from the excited singlet state of the amide anion in both acidic and basic environments.[21] For other examples of bioluminescence applications, the regeneration of an active semi-synthetic Aequorin, from Apoaequorin produced in cells and a coelenterazine analogue, is a key step in measuring $Ca^{2-}$ in cells. The relative rates of the regeneration of semi-synthetic Aequorins from Apoaequorin and synthetic coelenterazine analogs were compared[13a]. Another application is the detection of superoxide and peroxynitrite anion (ROS)[22]. ELISA, bioluminescence resonance energy transfer (BRET) can be used for protein interaction studies.[23,20]

In the original BRET technique, oxidation of coelenterazine 1 results in a $\lambda$=475 nm Rluc emission peak. Use of the coelenterazine derivative DeepblueC™ (also known as coelenterazine-400a, di-dehydro coelenterazine) results in a $\lambda$=395 nm Rluc emission peak.

Due to rapid development in molecular biological tools and recent development of extremely sensitive photon detectors, [24,7] Fluorescent imaging (FLI) and Bioluminescent imaging (BLI) can be applied to study cell and tissue specific promoters, but also to follow trafficking and fate of GFP and/or Luciferase expressing cells, apoptosis, protein-protein interaction and gene-transfer.[25]

The bioluminescent and chemiluminescent mechanisms are similar for coelenterazine but the conditions for eliciting each reaction are different. In bioluminescence, coelenterazine is the substrate for the photoprotein Aequorin and produces blue light in the presence of $Ca^{2+}$. On the other hand, chemiluminescent reactions of coelenterazine are typically performed in a purely chemical system with $O_2$ dissolved in an aprotic polar solvents such as dimethylsulfoxide (DMSO), dimethylformamide (DMF), and hexamethylphosphoramide (HMPA) in the presence or absence of bases (e.g., NaOH, t-BuOH, t-BuOK) or acetate buffer.[26]

Synthetic chemistry has played a key role in studying the luminescence properties of coelenterazine derivatives. The two synthetic approaches used to obtain 1 and its analogs are the "classical" synthesis[13d] and a more modern method which utilizes palladium coupling.[27,28,29,21] Further improved procedure was performed for an industrial approach.[30,31,32]

The present invention aims to solve several negative properties of the coelenterazine analogs present in the market. In particular, the structural modification proposed can be incorporated (easy variation in the synthesis procedure) into the known structures and selected to be the preferred compounds for both basic and industrial research (see Table 3).

TABLE 3

Known coelenterazine analogs present in the market

| | MW | R1 | R2 | R3 | λ max. Emission (nm) | Relative Luminescence capacity | Relative Intensity | Half-rise Time (s) (ms) |
|---|---|---|---|---|---|---|---|---|
| Coelenterazine Native | 423.50 | OH | OH | Phe | 465 | 1.00 | 1.00 | 0.4-0.8 |
| | | | | | | | | 6-30 ms |
| Coelenterazine cp | 415.48 | OH | OH | CP | 442 | 0.95 | 20 | 0.15-0.3 |
| | | | | | | 0.63 | 28 | 5 ms |
| Coelenterazine e | 449.50 | OH | OH | Phe | 405 and 465 | 0.5 | 4 | 0.15-0.3 |
| Coelenterazine f | 425.45 | F | OH | Phe | 473 | 0.80 | 18 | 0.4-0.8 |
| | | | | | | 0.80 | 20 | 6-30 ms |
| Coelenterazine fcp | 417.48 | F | OH | CP | 452 | 0.57 | 135 | 0.4-0.8 |
| Coelenterazine h | 407.50 | H | OH | Phe | 464 | 0.82 | 10 | 0.4-0.80 |
| | | | | | | 0.75 | 16 | 6-30 ms |
| Coelenterazine hcp | 399.49 | H | OH | CP | 444 | 0.67 | 190 | 0.15-0.3 |
| | | | | | | 0.65 | 500 | 2-5 ms |
| Coelenterazine i | 533.36 | I | OH | Phe | 476 | 0.70 | 0.03 | 8 |
| Coelenterazine ip | 389.45 | I | OH | 2P | 441 | 0.54 | 47 | 1 |
| Coelenterazine n | 457.52 | Naph | OH | Phe | 467 | 0.26 | 0.01 | 5 |
| | | | | | | 0.25 | 0.15 | 6-30 ms |
| Coelenterazine 2-methyl | 331.37 | | | | N/A | N/A | N/A | N/A |
| Coelenterazine 400a | 391.46 | | | | 400 | N/A | N/A | N/A |

Hydrogen (H), hydroxyl (OH), Phenyl (Phe), CycloPentyl (CP), 2-propionyl (2P), Naphthyl (Naph), methyl (Met). Coelenterazine-e has a —CH$_2$CH— bridge between the 6-phenyl-OH and position 5 of the imidazopyrazinone core.

The compounds of the invention are endowed with an improved red-shifted photoemission in bioluminescence while maintaining lipophilicity and enzymatic binding properties of the original coelenterazine molecules. Yet, the efficiency and sensibility to Ca$^{2-}$ depends on the interactions of the particular compound in the enzymatic binding pocket and the environment involved. Indeed, the bivalent sulfur and selenium atoms are bioisosteres of the methylene group. The present invention relates to new photochemical entity obtained by modification of the methylene (—CH$_2$—) in position C-8 of the imidazo[1,2-a]pyrazin-3(7H)-one nucleus, while the other substituents in position C-2, C-5 and C-6 are preserved (Formula 1).

BRIEF DESCRIPTION OF THE INVENTION

It has been found that the replacement of the methylene group (—CH$_2$—) bound to the C-8 atom of the imidazo[1,2-a]pyrazin-3(7H)-one nucleus of native coelenterazine 1 and its derivatives (Formula 1), with an hetero-atom gives unexpected and innovative properties to the molecules making their use in bio-chemiluminescence assays advantageous over existing molecules. In particular, the molecules allow the formation of emitting species with improved stability.

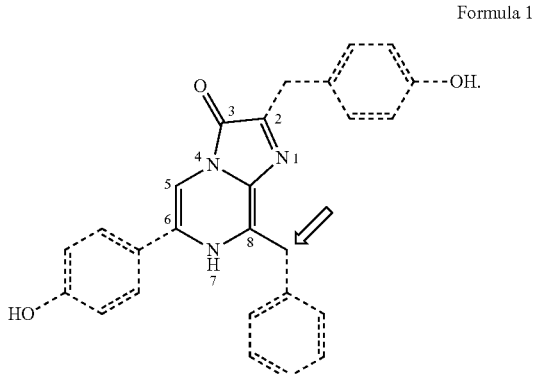

Formula 1

It is therefore an object of the present invention a compound of formula 1:

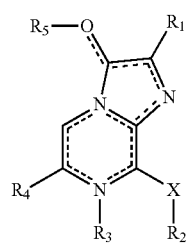

I wherein:

$R_1$ is a methyl, benzyl, 4-hydroxy-benzyl, 4-fluoro-benzyl, 4-iodio-benzyl or β-naphthylmethyl group;

$R_2$ is a methyl, phenyl, cyclopentyl, 2-propynyl, 4-fluoro-phenyl, 4-chloro-phenyl, 3-chloro-phenyl, 4-iodio-phenyl, 4-methyl-phenyl, 4-methoxy-phenyl, 4-hydroxy-phenyl, 3,5-bis-trifluoromethyl-phenyl, adamantyl, mercaptobenzyl, an Electron Withdrawing Group (EWG) or an Electron Donating Group (EDG);

$R_3$ is H or 0;

$R_4$ is a H, phenyl, 4-hydroxy-phenyl, 4-amino-phenyl, 4-methoxy-phenyl, 3-pyridinyl, 3,4-(methylendioxy)-phenyl, 2-methoxypyrimidin-5-yl, 4-acetoxy-phenyl or 4-(2,6 diaminohexanoyloxy)-phenyl;

$R_5$ is acetate, pivalate, pivaloyloxymethyl group or 0;

X is oxygen, sulfur, sulfoxide, nitrogen, selenium, iron, copper, cadmium or europium.

Preferably, $R_3$ is H and $R_5$ is 0, Still preferably, $R_2$ is a phenyl, cyclopentyl, 2-propynyl, 4-fluoro-phenyl, 4-chloro-phenyl, 4-methyl-phenyl, 4-methoxy-phenyl, 4-hydroxy-phenyl, adamantyl.

In a preferred embodiment the compound has the formula II:

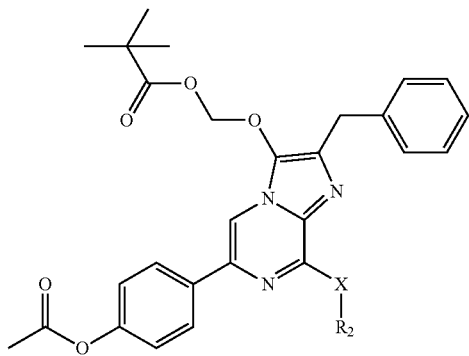

II wherein:

$R_2$ is a methyl, phenyl, cyclopentyl, 2-propynyl, 4-fluoro-phenyl, 4-chloro-phenyl, 3-chloro-phenyl, 4-iodio-phenyl, 4-methyl-phenyl, 4-methoxy-phenyl, 4-hydroxy-phenyl, 3,5-bis-trifluoromethyl-phenyl, adamantyl, mercaptobenzyl, an Electron Withdrawing Group (EWG) or an Electron Donating Group (EDG).

In a still preferred embodiment the compound has the formula III:

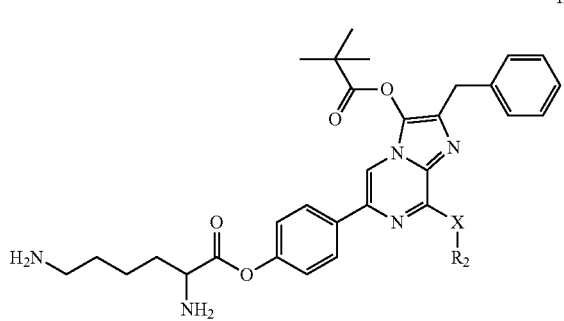

III wherein:

$R_2$ is a methyl, phenyl, cyclopentyl, 2-propynyl, 4-fluoro-phenyl, 4-chloro-phenyl, 3-chloro-phenyl, 4-iodio-phenyl, 4-methyl-phenyl, 4-methoxy-phenyl, 4-hydroxy-phenyl, 3,5-bis-trifluoromethyl-phenyl, adamantyl, mercaptobenzyl, an Electron Withdrawing Group (EWG) or an Electron Donating Group (EDG).

Still preferably, X is selenium or cadmium.

Preferred compounds are selected from the group of:

2-Benzyl-6-phenyl-8-(phenylthio)imidazo-[1,2-a]pirazin-3(7H)-one;

2-Benzyl-6-(4-hydroxyphenyl)-8-(phenylthio)imidazo[1,2-a]pyrazin-3(7H)-one;

2-Benzyl-8-(4-chlorophenylthio)-6-(4-hydroxyphenyl)imidazo[1,2-a]pyrazin-3(7H)-one;

2-Benzyl-6-(4-hydroxyphenyl)-8-(p-tolylthio)imidazo[1,2-a]pyrazin-3(7H)-one;

2-Benzyl-6-phenyl-8-(p-tolylthio)imidazo[1,2-a]pyrazin-3(7H)-one;

2-Benzyl-8-(4-methoxyphenylthio)-6-phenylimidazo[1,2-a]pyrazin-3(7H)-one;

2-Benzyl-8-(4-hydroxyphenylthio)-6-phenylimidazo[1,2-a]pyrazin-3(7H)-one;

2-Benzyl-8-(4-chlorophenylthio)-6-phenylimidazo[1,2-a]pyrazin-3(7H)-one;

2-Benzyl-6-phenyl-8-(4-fluorophenylthio)imidazo-[1,2-a]pirazin-3(7H)-one;

2-Benzyl-6-phenyl-8-(ciclopentylthio)imidazo-[1,2-a]pirazin-3(7H)-one;

2-Benzyl-6-phenyl-8-(adamantylthio)imidazo-[1,2-a]pirazin-3(7H)-one;

2-Benzyl-6-phenyl-8-phenoxyimidazo-[1,2-a]pirazin-3(7H)-one;

2-(4-Hydroxybenzyl)-8-(4-methoxyphenylthio)-6-phenylimidazo[1,2-a]pyrazin-3(7H)-one;

2-(4-Hydroxybenzyl)-8-(cyclopentylthio)-6-phenylimidazo[1,2-a]pyrazin-3(7H)-one;

2-(4-Hydroxybenzyl)-8-phenoxy-6-phenylimidazo[1,2-a]pyrazin-3(7H)-one;

2-Benzyl-6-phenyl-8-(phenylselanyl)imidazo-[1,2-a]pirazin-3(7H)-one;

2-Benzyl-6-(4-hydroxyphenyl)-8-(phenylselanyl)imidazo[1,2-a]pyrazin-3(7H)-one;

2-Benzyl-8-(4-chlorophenylselanyl)-6-(4-hydroxyphenyl)imidazo[1,2-a]pyrazin-3(7H)-one;

2-Benzyl-6-(4-hydroxyphenyl)-8-(p-tolylselanyl)imidazo[1,2-a]pyrazin-3(7H)-one;

2-Benzyl-6-phenyl-8-(p-tolylselanyl)imidazo[1,2-a]pyrazin-3(7H)-one;

2-Benzyl-8-(4-methoxyphenylselanyl)-6-phenylimidazo[1,2-a]pyrazin-3(7H)-one;

2-Benzyl-8-(4-hydroxyphenylselanyl)-6-phenylimidazo[1,2-a]pyrazin-3(7H)-one;

2-Benzyl-8-(4-chlorophenylselanyl)-6-phenylimidazo[1,2-a]pyrazin-3(7H)-one;

2-Benzyl-6-phenyl-8-(4-fluorophenylselanyl)imidazo-[1,2-a]pirazin-3(7H)-one;

2-Benzyl-6-phenyl-8-(ciclopentylselanyl)imidazo-[1,2-a]pirazin-3(7H)-one;

2-Benzyl-6-phenyl-8-(adamantylselanyl)imidazo[1,2-a]pirazin-3(7H)-one;

2-(4-Hydroxybenzyl)-8-(4-methoxyphenylselanyl)-6-phenylimidazo[1,2-a]pyrazin-3(7H)-one;

2-(4-Hydroxybenzyl)-8-(cyclopentylselanyl)-6-phenylimidazo[1,2-a]pyrazin-3(7H)-one;

(2-Benzyl-3-oxo-6-phenyl-3,7-dihydroimidazo[1,2-a]pyrazin-8-yl)(phenyl)cadmium;

(2-Benzyl-6-(4-hydroxyphenyl)-3-oxo-3,7-dihydroimidazo
  [1,2-a]pyrazin-8-yl)(phenyl)cadmium;
(2-Benzyl-6-(4-hydroxyphenyl)-3-oxo-3,7-dihydroimidazo
  [1,2-a]pyrazin-8-yl)(4-chlorophenyl)cadmium;
(2-Benzyl-6-(4-hydroxyphenyl)-3-oxo-3,7-dihydroimidazo
  [1,2-a]pyrazin-8-yl)(p-tolyl)cadmium;
(2-Benzyl-3-oxo-6-phenyl-3,7-dihydroimidazo[1,2-a]
  pyrazin-8-yl)(p-tolyl)cadmium;
(2-Benzyl-3-oxo-6-phenyl-3,7-dihydroimidazo[1,2-a]
  pyrazin-8-yl)(4-methoxyphenyl)cadmium;
(2-Benzyl-3-oxo-6-phenyl-3,7-dihydroimidazo[1,2-a]
  pyrazin-8-yl)(4-hydroxyphenyl)cadmium;
(2-Benzyl-3-oxo-6-phenyl-3,7-dihydroimidazo[1,2-a]
  pyrazin-8-yl)(4-chlorophenyl)cadmium;
(2-Benzyl-3-oxo-6-phenyl-3,7-dihydroimidazo[1,2-a]
  pyrazin-8-yl)(4-fluorophenyl)cadmium;
(2-Benzyl-3-oxo-6-phenyl-3,7-dihydroimidazo[1,2-a]
  pyrazin-8-yl)(cyclopentyl)cadmium or
(2-(4-Hydroxybenzyl)-3-oxo-6-phenyl-3,7-dihydroimidazo
  [1,2-a]pyrazin-8-yl)(phenyl)cadmium.

It is a further object of the invention a composition comprising the compound according to the invention and excipients or diluent or carriers.

It is a further object of the invention the use of the compounds as described above or of the composition of the invention as a chemiluminescent and/or bioluminescent reagent.

Preferably, the use is for superoxide and/or peroxynitrite anion detection.

It is a further object of the invention the use of the compounds as described above or of the composition of the invention as a substrate of a luciferase protein system.

Preferably, the luciferase protein system belongs to the group of: *Renilla, Aequorea, Obelia*, or *Gaussia* and their mutated, synthetic or semi-synthetic analogues.

It is a further object of the invention a chemiluminescent and/or bioluminescent assay comprising the step of exposing a sample to the compound of the invention as described above or of the composition of the invention.

Preferably the assay is an Enzyme-Linked ImmunoSorbent Assay.

It is a further object of the invention a kit for performing a chemiluminescent and/or bioluminescent assay comprising the compound of the invention or the composition of the invention.

The invention will be now illustrated by means of non limiting examples referring to the following figures.

DETAILED DESCRIPTION OF THE INVENTION

It has been demonstrate that the substitution of the methylene group ($—CH_2—$) bound to the C-8 of the imidazo[1,2-a]pyrazin-3(7H)-one nucleus (Formula 1) with an heteroatom, gives a particular stability to the emitting species, probably due to the amide-anion form. The introduced modification brings to a particular electron-rich structure (FIG. 2), which has interesting electrical conductance properties. While similar simplified structures were investigated for their CIEEL (Chemically Initiated Electron Exchange Luminescence) properties in the 1,4-dioxy biradical intermediates species,[33a] or for their use as potential organic conducting materials,[33b] the invention allows to consider this electron-rich structure from a different point of view. Indeed, the bio-chemiluminescent properties of the imidazo[1,2-a]pyrazin-3(7H)-one scaffold taken together with the above-mentioned structure, characterize an interesting novel photochemical system, named "2YG" (see Scheme 3), with other possibilities to allocate excited electrons in different energy levels.

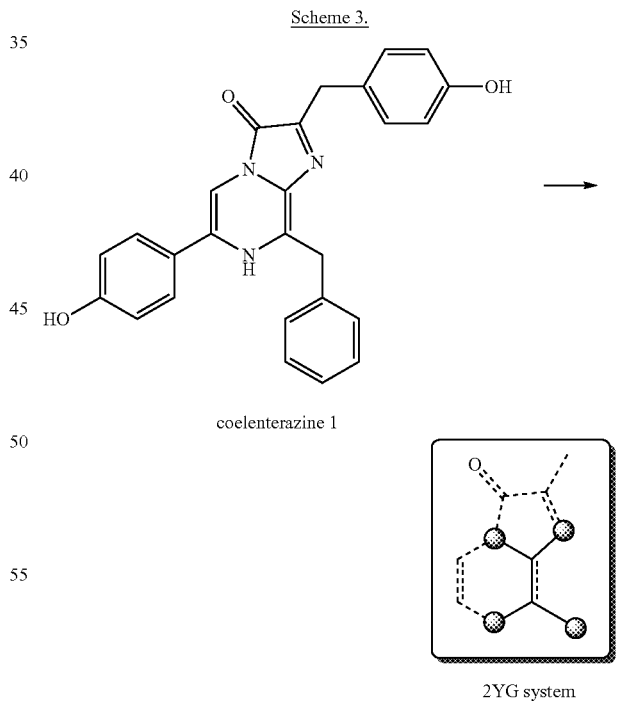

Scheme 3.

coelenterazine 1

2YG system

That is probably due to the combination of inductive/resonance stabilization of the emitting intermediate, which has an extended electron skeleton, producing a hybrid of the excited state of lower energy. The resulting light emission will be modulated with longer wavelength (bathochromic shift).

Figure 1:
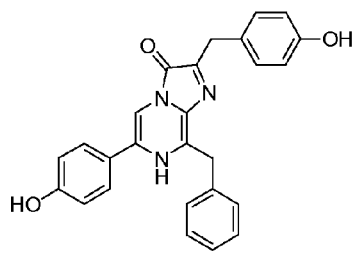
FIG. 1: Example of known structure 1-4.
Figure 1:
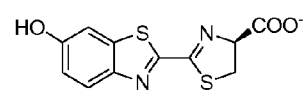
Figure 1:
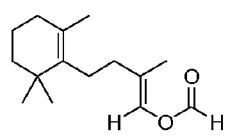
Figure 1:
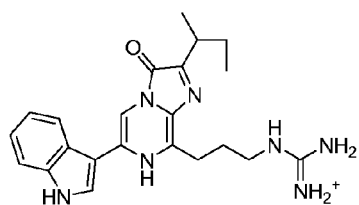
Figure 2:
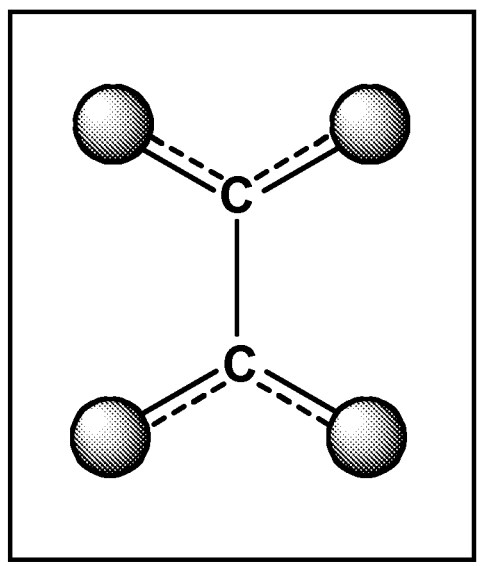
FIG. 2: Electron-rich structure. The spheres represent generic heteroatoms, in the 2YG system, as shown in scheme 3 below, three of them are nitrogen atoms: N-1, N-4, N-7 of the original imidazo[1,2-a]pyrazin-3(7H)-one nucleus.

In FIG. 2, the spheres represent generic heteroatoms, in the 2YG system three of them are nitrogen atoms: N-1, N-4, N-7 of the original imidazo[1,2-a]pyrazin-3(7H)-one nucleus (see Scheme 3).

The bio and chemiluminescence of the 2YG system are also due to the nature of the heteroatoms covalently bound to the C-8 of the imidazo[1,2-a]pyrazin-3(7H)-one nucleus. The choice of the hetero-atoms depends on the chemical and physical characteristics of the atom (e.g. electronegativity and dimension, molecular orbitals involved, valence and electronic shell configurations) and the presence of well-known procedures in organic synthesis to obtain the derivatives.

The nature of the substituents bound to the heteroatom can influence the bio-chemiluminescence's of the analogs. In particular, atoms or groups of atoms can add or withdraw electron density to a system. Electron Withdrawing Groups (EWG, such as halogen, aldheyde, ketone, trifluoromethyl, nitrile, nitrogen dioxide functional groups . . . ) remove electron density from a system and tend to stabilize anions or electron rich structures. Conversely, EWG destabilize cations or electron poor structures. Electron Donating Groups (EDG, such as hydroxy, amine, ether, amide, ester, phenyl, alkyl, alkenyl functional groups . . . ) add electron density to a system and tend to stabilize cations or electron poor systems. Conversely, EDG destabilize anions or electron rich systems.

The simplicity of the invention allows to predict negligible effects on other chemical properties of the derivatives, hydrophobic properties (cells membrane crossing), common organic solvents solubility and stability.

Chemistry.

2-Aminopyrazine derivatives 14a-e were synthesized following the procedure described in Scheme 4.

TABLE 4

Compounds 14a-e.

| Comp. | Ar |
|---|---|
| 14a | 4-methoxyphenyl |
| 14b | 4-methylphenyl |
| 14c | 6-methyl-1,3-benzodioxol-5-yl |
| 14d | 5-methylpyridin-3-yl |
| 14e | 4-(BOC-amino)-methylphenyl |

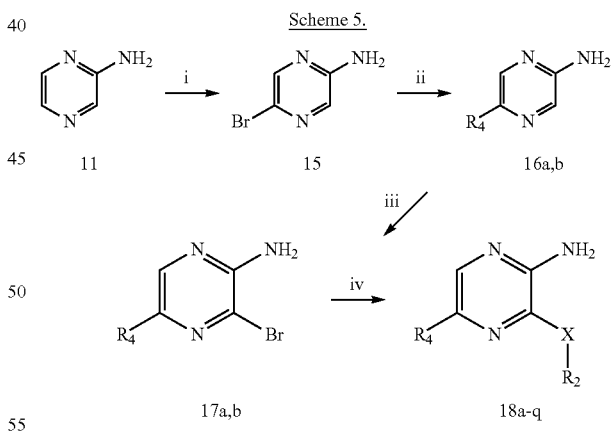

The synthesis of the pyrazine derivatives with different substituents in position 3 of the pyrazinc ring 18a-q is reported in Scheme 5.

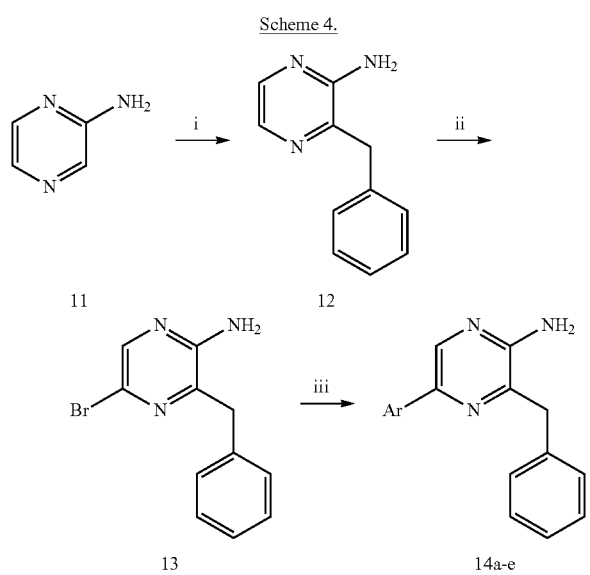

Scheme 4.

Reagents: i) Toluene, n-butylithium, TMEDA, THF; ii) tetra-n-butylammonium tribromide, pyridine, CHCl₃; iii) ArB(OH)₂, BINAP, Pd(OAc)₂, Cs₂CO₃, toluene/EtOH (1:1).

Reagents: i) NBS, CH₂Cl₂; ii) R₄B(OH)₂, Pd(OAc)₂, BINAP, Cs₂CO₃, toluene/EtOH (1:1); iii) Br₂, pyridine, CHCl₃; iv) C₆H₅XH, 4-ClC₆H₄SH, 4-FC₆H₄SH, 4-CH₃C₆H₄SH, 4-CH₃OC₆H₄SH, 3,5-Bis-CF₃—C₆H₄SH, CH₃SH, Cyclopentanethiol, 1-Adamantanethiol, 2-Mercaptobenzothiazole, NaH, anhydrous DMF or ACN.

2-Aminopyrazine (11) was converted into the 2-amino-3-benzylpyrazine (12) by means of direct alkylation with benzyllithium in THF.[32] Pyrazine derivative 12 was selectively brominated in position 5 with tetra-n-butylammonium tribromide, to obtain bromoderivate 13[29] used for the Suzuki coupling[27b] with the appropriate boronic acids, to obtain the derivatives 14a-e (see Table 4).

2-Aminopyrazine (11) was treated with N-bromosuccinimide (NBS) in dichloromethane to obtain bromoderivative 15,[34] which was used in a Suzuki coupling to afford 2-aminopyrazine derivatives 16a,b. These compounds were then treated with bromine (Br₂) in a mixture of chloroform and pyridine to get the 3-bromoderivatives 17a,b in good yield.[35] Derivatives 18a-q, were obtained from the bromoderivatives 17a,b by reaction with appropriate thiol (or phenol) derivatives and sodium hydride in anhydrous DMF (or anhydrous ACN).36

TABLE 5

Compounds 18a-q.

| Comp. | R$_4$ | R$_2$ | X |
|---|---|---|---|
| 18a | 4-methoxyphenyl | Phenyl | S |
| 18b | Phenyl | Phenyl | S |
| 18c | 4-methoxyphenyl | 4-chlorophenyl | S |
| 18d | 4-methoxyphenyl | 3,5-bis(trifluoromethyl)phenyl | S |
| 18e | 4-methoxyphenyl | 4-methylphenyl | S |
| 18f | 4-methoxyphenyl | 4-methoxyphenyl | S |
| 18g | 4-methoxyphenyl | Methyl | S |
| 18h | 4-(Boc-amino)phenyl | Phenyl | S |
| 18i | Phenyl | 4-methylphenyl | S |
| 18j | Phenyl | 4-methoxyphenyl | S |
| 18k | Phenyl | 3,5-bis(trifluoromethyl)phenyl | S |
| 18l | Phenyl | 4-chlorophenyl | S |
| 18m | Phenyl | 4-fluorophenyl | S |
| 18n | Phenyl | cyclopentyl | S |
| 18o | Phenyl | adamantyl | S |
| 18p | Phenyl | benzothiazol-2-yl | S |
| 18q | Phenyl | Phenyl | O |

Oxidation of the thioether 18b with oxone in methanol afforded compound 19 (Scheme 6).[37]

Scheme 6.

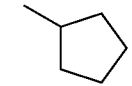

Reagents: i) oxone, MeOH

The protecting O-methyl group of derivatives 14a and 18a, c-e was removed by reaction with pyridine hydrochloride at 190° C.,[30] to obtain the corresponding hydroxyl derivatives 20a-e (Scheme 7).

Scheme 7.

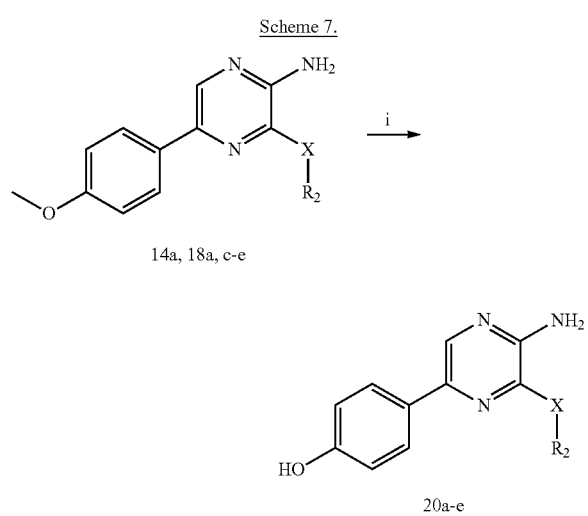

X = CH$_2$, S
Reagents: i) pyridine•HCl, 190° C.

On the other hand, 4-methoxyphenylthioderivative 18j was converted into the corresponding 4-hydroxyphenyl derivative 18r by using a 1.0M solution of BBr$_3$ in dichloromethane as reported in Scheme 7bis.

Scheme 7bis.

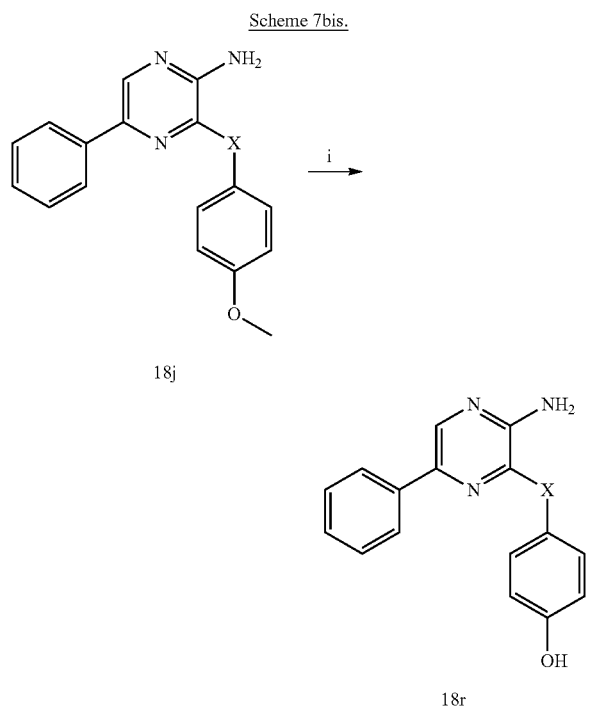

Reagents: i) BBr$_3$, CH$_2$Cl$_2$.

The final steps of the synthesis of the target bicyclic derivatives (compounds 23 and 25) are reported in Scheme 8 and 8bis. Diethoxy derivative 22 (Scheme 8) was obtained by reaction of the commercially available Grignard reagent 21 with ethyl diethoxyacetate in THF[38].

Scheme 8.

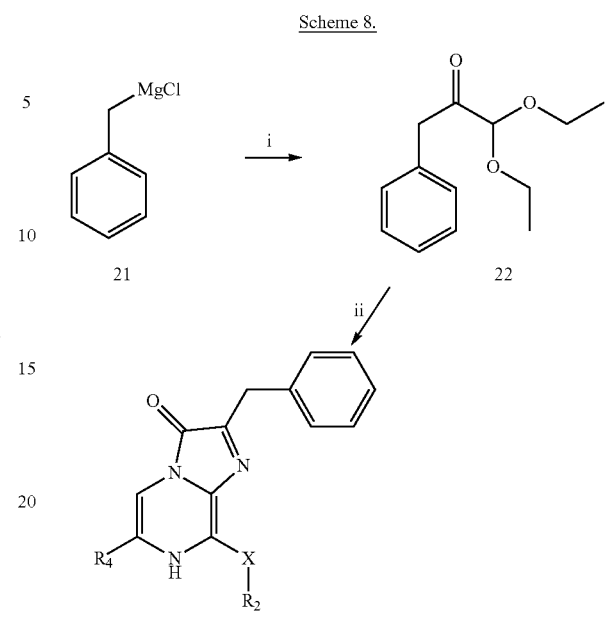

Reagents: i) ethyl diethoxyacetate, THF anh; ii) 14a-e, 18a-f,h-q and 19, 20a-e, HCl conc., EtOH.

Synthon 22 was then condensed with aminopyrazine intermediates 14a-e, 18a-f,h-r, 19 and 20a-e in the presence of ethanol and concentrated HCl to afford target compounds 23a-r (see Table 6).

TABLE 6

Compounds 23a-r.

| Comp. | R$_4$ | X | R$_2$ |
|---|---|---|---|
| 23a | 4-HO-C$_6$H$_4$ | —CH$_2$— | C$_6$H$_5$ |
| 23b | C$_6$H$_5$ | —CH$_2$— | C$_6$H$_5$ |
| 23c | 4-H$_2$N-C$_6$H$_4$ | —CH$_2$— | C$_6$H$_5$ |
| 23d | 4-H$_3$CO-C$_6$H$_4$ | —CH$_2$— | C$_6$H$_5$ |
| 23e | benzo[1,3]dioxol-5-yl | —CH$_2$— | C$_6$H$_5$ |
| 23f | C$_6$H$_5$ | —S— | C$_6$H$_5$ |

TABLE 6-continued

Compounds 23a-r.

| Comp. | R4 | X | R2 |
|---|---|---|---|
| 23g | 4-HO-C6H4-CH2- | —S— | C6H5-CH2- |
| 23h | 4-H2N-C6H4-CH2- | —S— | C6H5-CH2- |
| 23i | 4-HO-C6H4-CH2- | —S— | 4-Cl-C6H4-CH2- |
| 23j | 4-HO-C6H4-CH2- | —S— | 4-CH3-C6H4-CH2- |
| 23k | C6H5-CH2- | —S— | 4-CH3-C6H4-CH2- |
| 23l | C6H5-CH2- | —S— | 4-CH3O-C6H4-CH2- |
| 23m | C6H5-CH2- | —S— | 4-HO-C6H4-CH2- |
| 23n | C6H5-CH2- | —S— | 4-Cl-C6H4-CH2- |
| 23o | C6H5-CH2- | —S— | 4-F-C6H4-CH2- |
| 23p | C6H5-CH2- | —S— | cyclopentyl-CH2- |
| 23q | C6H5-CH2- | —S— | adamantyl-CH2- |
| 23r | C6H5-CH2- | —O— | C6H5-CH2- |

Scheme 8bis.

Compounds of formula 24a-c as indicated below were obtained via known synthesis pathways as described in literature using compounds 18j,n,q as starting material.

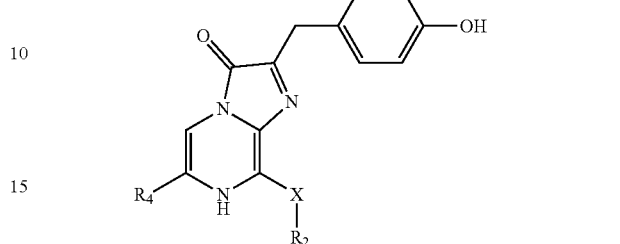

24a-c

Scheme 9.

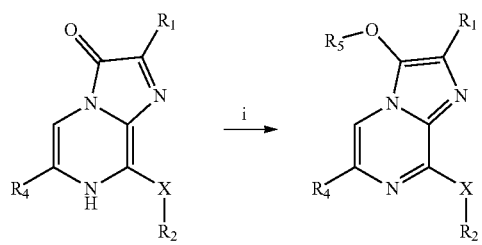

23l,p → 25a,b

Reagents: i) Acetyl chloride, DMAP, CH2Cl2.

Reagents: i) Acetyl chloride, DMAP, CH2Cl2.

Compounds 23l,p were also converted to the corresponding acetyl derivative 25a,b by means of reaction with Acetyl chloride in presence of DMAP (Scheme 9).

EXAMPLES

All chemicals used were of reagent grade. Yields refer to purified products and are not optimized. Melting points were determined in open capillaries on a Gallenkamp apparatus and are uncorrected. Merck silica gel 60 (230-400 mesh) and Aluminium oxide neutral 90 (70-230 mesh) were used for column chromatography. Merck TLC plates, silica gel 60 F254 and Aluminium oxide 60 F254 were used for TLC. $^1$H-NMR spectra were recorded with a Bruker AC 200 and Bruker DRX 400 ADVANCE spectrometers in the indicated solvents (TMS as internal standard): the values of the chemical shifts are expressed in ppm and the coupling constants (J) in Hz. Mass spectra were recorded on either a Varian Saturn 3 spectrometer or a ThermoFinnigan LCQ-Deca. HPLC analysis were performed with a VWR PUMP L2130, with a column LiChroCART 125-4 (stationary phase Purospher STAR RP-18).

2-Amino-3-benzylpyrazine (12)

To a mixture of N,N,N',N'-tetramethylethylendiamine (TMEDA, 15.00 mL, 0.10 mol) in toluene (22.00 mL, 0.21 mol) at 0° C., buthyllitium 1.6M in n-hexane (63.00 mL, 0.10 mol) was added dropwise. Then the mixture was heated at 60° C. and after 30 min was slowly added to a cooled solution of 2-aminopyrazine 11 (2.00 g, 0.02 mol) in anhydrous THF (20 mL). The reaction mixture was stirred at 0° C. for 30 min, poured into ice and extracted with ethyl acetate (3×20 mL). The organic layer was dried over $Na_2SO_4$, filtered and the solvent removed under reduced pressure. The crude was purified by flash chromatography (EtOAc, dichloromethane; 65:35) to get 1.38 g (35% yield) of the title compound 12 as a yellow solid (mp 93-96° C.). $^1$H-NMR ($CDCl_3$): 4.08 (s, 2H), 4.33 (br s, 2H), 7.18-7.35 (m, 5H), 7.91 (m, 2H). MS (ESI): m/z 186 (M+H$^-$).

2-Amino-3-benzyl-5-bromopyrazine (13)

Figure 3:
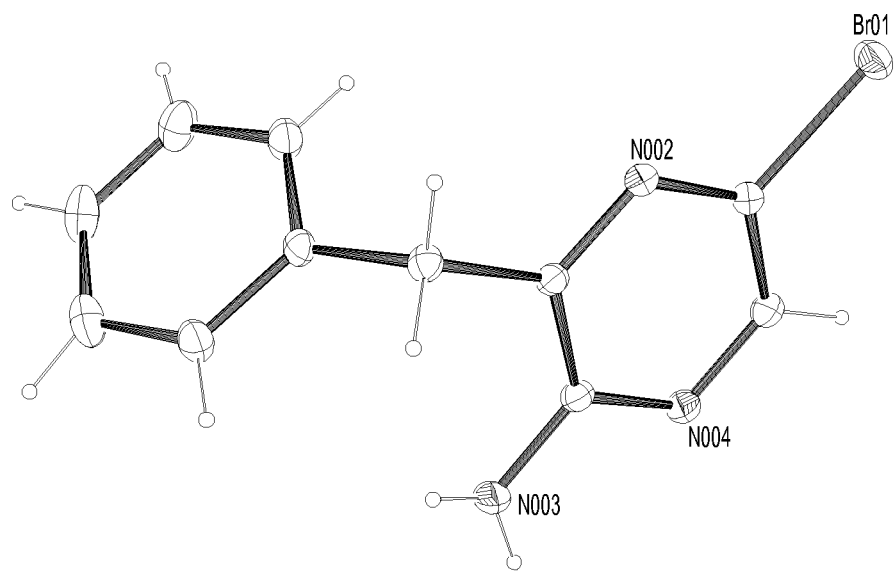
FIG. 3: Crystallography of compound 13.

To a solution of 3-benzyl-2-aminopyrazine 12 (1.38 g, 7.40 mmol) in chloroform (40 mL), pyridine (1.80 mL, 22.00 mmol) and tetrabutylamoniumtribromide TBATB (3.57 g, 7.40 mmol) were added at room temperature. After 1 h the reaction mixture was washed with 20% aqueous solution of NaCl, the organic layer was then dried over $Na_2SO_4$, filtered and the solvent removed under reduced pressure. The crude was purified by flash chromatography (EtOAc-dichloromethane, 80:20) to get 1.75 g (89% yield) of the title compound 13 as a pale brown solid and subsequent recrystallization (n-exane/diethyl ether) gave colorless crystals suitable for crystallographic studies. $^1$H-NMR ($CDCl_3$): 3.97 (s, 2H), 4.74 (br s, 2H), 7.10-7.24 (m, 5H), 7.89 (s, 1H). MS (ESI): m/z 265 (M+H). The crystallography of compound 13 is shown in FIG. 3, demonstrating its purity.

2-Amino-5-bromopyrazine (15)

To a cooled solution of 2-aminopyrazine 11 (2.00 g, 21.00 mmol) in dichloromethane (50 mL) N-bromosuccinimide (NBS) (3.73 g, 21.00 mmol) was added in portion. The mixture was stirred at 0° C. for 2 h and washed with $Na_2CO_3$ s.s. and water, the organic layer was dried over $Na_2SO_4$, filtered and the solvent removed under reduced pressure to get 2.80 g of the title compound 15 (77% yield) as an orange solid without further purification (mp 105-110° C.). $^1$H-NMR ($CDCl_4$): 4.61 (br s, 2H), 7.75 (s, 1H), 8.07 (s, 1H). MS (GC-MS): m/z 174.

General Procedures of the Suzuki Coupling for the Synthesis of Compounds 14a-e, 16a,b.

Method A:[39]

A mixture of 2,2"-bis(diphenilphosphino)-1,1"-binaphtyl (BINAP) (0.20 mmol) and palladium diacetate (Pd(OAc)$_2$) (0.1 mmol) in 5 mL of toluene/ethanol (1:1) was heated at 80° C. for 30 min. To a solution of the appropriate boronic acid (4 mmol) in 5 mL of toluene/ethanol (1:1), cesium carbonate ($Cs_2CO_3$) (6.0 mmol) was added and the resulting solution was degassed with Argon. Then the solution of the catalyst, 2-amino-3-benzyl-5-bromopyrazine 13 or 2-amino-5-bromopyrazine 15 ((2.0 mmol) were added in rapid sequence. The resulting mixture was heated to reflux for 5-20 h, depending on the boronic acid used. The solvent was then removed and the crude recovered with EtOAc, washed with water. The organic layer was dried over $Na_2SO_4$, filtered and the solvent removed under reduced pressure.

Method B

A mixture of triphenylphosphine (PPh$_3$) (0.15 mmol) and palladium diacetate (Pd(OAc)$_2$) (0.04 mmol) in anhydrous acetonitrile (3 mL) was heated at 60° C. for 30 min. To a solution of the appropriate boronic acid (0.90 mmol) in acetonitrile (3 mL), 0.4M solution $Na_2CO_3$ (1 mL) was added. Then the solution of the catalyst, 2-amino-3-benzyl-5-bromopyrazine 13 or 2-amino-5-bromopyrazine 15 (0.75 mmol) were added in rapid sequence. The resulting mixture was heated at reflux for 5-20 h, depending on the boronic acid of the reaction. Solvent was then removed and the crude recovered with EtOAc, washed with water, the organic layer was dried over $Na_2SO_4$, filtered and the solvent removed under reduced pressure. The purification of the crude was done by flash chromatography (eluent reported in the compound description) to get the desired compound 14a-e, 16a,b.

2-Amino-3-benzyl-5-(4-methoxyphenyl)pyrazine (14a)

The compound was purified by flash chromatography using a mixture of dichloromethane-EtOAc (90:10 v/v) as eluent, to get 0.14 g of the title compound 14a as a beige solid (66% yield) and subsequent recrystallization (n-exane/diethyl ether) gave crystals suitable for crystallographic studies (mp 150-153° C.). $^1$H-NMR ($CDCl_3$): 3.84 (s, 3H), 4.16 (s, 2H), 4.31 (br s, 2H), 6.97 (d, J=8.8, 2H), 7.24-7.34 (m, 5H), 7.87 (d, J=8.8, 2H), 8.32 (s, 1H). MS (ESI):m/z 292 (M+H$^+$).

Figure 4:
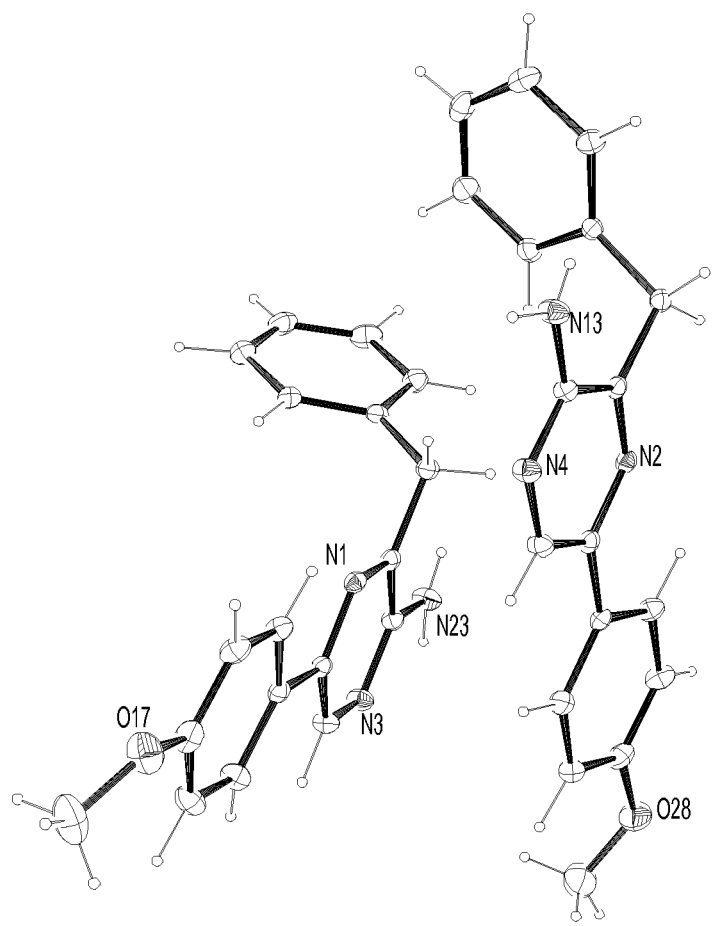
FIG. 4: Crystallography of compound 14a as a dimer.

The crystallography of compound 14a as a dimer is shown in FIG. 4, demonstrating its purity.

2-Amino-3-benzyl-5-phenylpyrazine (14b)

The compound was purified by flash chromatography using a mixture of petroleum ether-EtOAc (70:30 v/v) to get 0.12 g of the title compound 14b as a yellow oil (61% yield). $^1$H-NMR ($CDCl_3$): 4.15 (s, 2H), 4.38 (br s, 2H), 7.22-7.46 (m, 8H), 7.89-7.93 (m, 2H), 8.37 (s, 1H). MS (ESI): m/z 262 (M+H$^+$).

2-Amino-3-benzyl-5-[3,4-(methylendioxy)-phenyl]pyrazine (14c)

The compound was purified by flash chromatography using a mixture of dichloromethane-EtOAc (90:10 v/v) to get 0.12 g of the title compound 14c as an orange solid (mp 132-135° C., 52% yield). $^1$H-NMR ($CDCl_3$): 4.15 (s, 2H), 4.34 (s, 2H), 5.98 (s, 2H), 6.87 (d, J=8.2, 1H), 7.24-7.32 (m, 5H), 7.39-7.41 (m. 1H), 7.44 (s, 1H), 8.28 (s, 1H). MS (ESI): m/z 306 (M+H$^+$).

2-Amino-3-Benzyl-5-(3-pyridin)pyrazine (14d)

The compound was purified by flash chromatography using a mixture of dichloromethane-EtOAc (5:95 v/v) to get 0.08 g of the title compound 14d as a pale yellow solid (mp 150-153° C., 38% yield). $^1$H-NMR ($CDCl_3$): 4.17 (s, 2H), 4.55 (s, 2H), 7.23-7.38 (m, 6H), 8.19-8.25 (m, 1H), 8.39 (s, 1H), 8.56-8.59 (m, 1H), 9.14 (s, 1H). MS (ESI): m/z 263 (M+H$^-$).

tert-Butyl 4-(5-amino-6-benzylpyrazin-2-yl)phenylcarbamate (14e)

The compound was purified by flash chromatography using a mixture of dichloromethane-EtOAc (1:1 v/v) to get 0.16 g of the title compound 14e as a brown oil (65% yield). $^1$H-NMR ($CD_3OD$): 1.55 (s, 9H), 4.15 (s, 2H), 7.19-7.32 (m, 5H), 7.48 (d, J=8.7, 2H), 7.81 (d, J=8.7, 2H), 8.27 (s, 1H). MS (ESI): m/z 377 (M+H$^+$).

2-Amino-5-(4-methoxyphenyl)pyrazine (16a)

The compound was purified by flash chromatography using a mixture of dichloromethane-EtOAc (1:1 v/v) to obtain 0.37 g of the title compound 16a as a yellow solid (mp 157-159° C., 90% yield). $^1$H-NMR (CDCl$_3$): 3.84 (s, 3H), 4.59 (br s, 2H), 6.97 (d, J=8.8, 2H), 7.79 (d, J=8.7, 2H), 8.04 (s, 1H).8.37 (s, 1H). MS (ESI): m/z 202 (M+H$^+$).

2-Amino-5-phenylpyrazine (16b)

The compound was purified by flash chromatography using a mixture of dichloromethane-EtOAc (50:50 v/v) to obtain 0.90 g of the title compound 16b as a yellow solid (mp 136-139° C., 92% yield). $^1$H-NMR (CDCl$_3$): 4.62 (br s, 2H), 7.34-7.44 (m, 3H), 7.84-7.86 (m, 2H), 8.04 (s, 1H), 8.44 (s, 1H). MS (GC-MS): m/z 171.

2-Amino-3-bromo-5-(4-methoxyphenyl)pyrazine (17a)

To a solution of 2-amino-5-(4-methoxyphenyl)pyrazine 16a (0.35 g, 1.7 mmol) and pyridine (0.20 mL, 2.6 mmol) in chloroform (20 mL), bromine (Br$_2$) (0.13 mL, 2.6 mmol) was added dropwise in chloroform (3 mL) at −10° C. After 6 h stirring at room temperature, the reaction mixture was washed with water, the organic layer dried over Na$_2$SO$_4$, filtered and the solvent was removed under reduced pressure. The crude product was purified by flash chromatography using dichloromethane-EtOAc (90:10 v/v) as eluent, to obtain 0.33 g of 17a as an brown solid (mp 166-170° C., 70% yield). $^1$H-NMR (CDCl$_3$): 3.83 (s, 3H), 5.04 (br s, 2H), 6.92-6.96 (m, 2H), 7.76-7.80 (m, 2H), 8.31 (s, 1H). GC-MS (EI): m/z 279,281 (M$^1$, 100).

2-Amino-3-Bromo-5-phenylpyrazine (17b)

To a solution of 2-amino-5-phenylpyrazine 16b (0.90 g, 5.20 mmol) and pyridine (0.40 mL, 5.00 mmol) in chloroform (20 mL) bromine (Br$_2$) (0.25 mL, 4.90 mmol) was added dropwise in chloroform (3 mL) at −10° C. After 18 h stirring at room temperature, the reaction mixture was washed with water, the organic layer dried over Na$_2$SO$_4$, filtered and the solvent was removed under reduced pressure. The crude product was purified by flash chromatography using dichloromethane-EtOAc (90:10 v/v) as eluent, to obtain 0.87 g of 17b as an orange solid (mp 148-152° C., 67% yield). $^1$H-NMR (CDCl$_3$): 5.04 (br s, 2H), 7.31-7.46 (m, 3H), 7.84-7.87 (m, 2H), 8.39 (s, 1H). MS (GC-MS): m/z 250.

2-Amino-5-(4-methoxyphenyl)-3-phenylthiopyrazine (18a)

To a cooled solution of thiophenol (0.08 mL, 0.7 mmol) in dry DMF (10 mL), sodium hydride (NaH) (0.025 g, 1.00 mmol) was added and the resulting mixture was stirred for 15 min at 5-10° C. After this time 2-amino-3-bromo-5-(4-methoxyphenyl)pyrazine 17a (0.20 g, 0.71 mmol) was added and the mixture refluxed for 6 h, cooled and extracted with EtOAc. The organic layer was washed with water, dried over Na$_2$SO$_4$, filtered and the solvent removed under reduced pressure to get a crude that was purified by flash chromatography using petroleum ether-EtOAc (65:45 v/v) as eluent, to obtain 0.15 g of the title compound 18a as an orange solid (mp 89-90° C., 70% yield). $^1$H-NMR (CDCl$_3$): 3.81 (s, 3H), 4.90 (br s, 2H), 6.89 (d, J=8.7, 2H), 7.33-7.39 (m, 7.45-7.50 (m, 2H), 7.69 (d, J=8.7, 2H), 8.28 (s, 1H). MS (ESI): m/z 310 (M+H$^+$).

2-Amino-5-phenyl-3-phenylthiopyrazine (18b)

To a cooled solution of thiophenol (0.10 mL, 1.00 mmol) in dry DMF (10 mL), sodium hydride (NaH) (0.025 g, 1.00 mmol) was added the resulting mixture was stirred for 15 min at 5-10° C. After this time 2-amino-3-bromo-5-phenylpyrazine 17b (0.25 g, 1.00 mmol) was added and the mixture refluxed for 20 h, cooled and extracted with EtOAc. The organic layer was washed with water, dried over Na$_2$SO$_4$, filtered and the solvent removed under reduced pressure to get a crude that was purified by flash chromatography using petroleum ether-EtOAc (60:40 v/v) as eluent, to obtain 0.22 g of the title compound 18b as a brown solid (mp 109-112° C., 79% yield). $^1$H-NMR (CDCl$_3$): 4.92 (br s, 2H), 7.29-7.50 (m, 8H), 7.74-7.77 (m, 2H), 8.35 (s, 1H). MS (ESI): m/z 280 (M+H$^1$).

2-Amino-5-(4-methoxyphenyl)-3-(4-chlorophenyl) thiopyrazine (18c)

To a solution of 4-chlorophenylthiol (0.25 g, 1.7 mmol) in dry DMF (10 mL), sodium hydride (NaH) (0.06 g, 2.5 mmol) was added and the resulting mixture was stirred for 15 min. After this time 2-amino-3-bromo-5-(4-methoxyphenyl)pyrazine 17a (0.12 g, 0.4 mmol) was added and the resulting mixture was heated at 110° C. for 18 h. The solution was concentrated under reduced pressure and the crude was taken in Ethyl Acetate and washed with water. Then the organic layer was anidrified over Na$_2$SO$_4$, filtered and the solvent removed under reduced pressure to get a crude that was purified by flash-chromatography using chloroform-methanol (95:5) to get 0.11 g of title compound 18c as a yellow solid (mp 154-155° C., yield 74%). $^1$H-NMR (CDCl$_3$): 3.82 (s, 3H); 4.89 (br s, 2H), 6.87-6.94 (m, 2H), 7.22-7.46 (m, 4H), 7.63-7.71 (m, 2H), 8.28 (s, 1H). MS (ESI): m/z 366, 368 (M+Na$^+$).

2-Amino-5-(4-methoxyphenyl)-3-(3,5-bis-trifluoromethylphenyl)thiopyrazine (18d)

To a solution of 3,5-bis-trifluoromethylphenylthiol (0.03 mL, 0.18 mmol) in dry DMF (5 mL), sodium hydride (NaH) (0.01 mg, 0.4 mmol) was added and the resulting mixture was stirred for 15 min. After this time 2-amino-3-bromo-5-(4-methoxyphenyl)pyrazine 17a (0.05 g, 0.18 mmol) was added and the resulting mixture was heated at 110° C. for 4.5 h. The solution was concentrated under reduced pressure and the crude was taken in Ethyl Acetate and washed with water. Then the organic layer was anidrified over Na$_2$SO$_4$, filtered and the solvent removed under reduced pressure to get a crude that was purified by Al$_2$O$_3$ chromatography using EtOAc to get 0.04 g of title compound 18d as a pale brown solid (mp 136-138° C., yield 50%). $^1$H-NMR (CDCl$_3$): 3.82 (s, 3H), 4.93 (br s, 2H), 6.89 (d, J=9.2, 2H), 7.65 (d, J=9.2, 2H), 7.86 (s, 1H), 8.04 (s, 2H), 8.32 (s, 1H). MS (ESI): m/z 446 (M+H$^+$).

2-Amino-5-(4-methoxyphenyl)-3-(4-methylphenyl) thiopyrazine (18e)

To a solution of 4-methylphenylthiol (0.07 g, 0.54 mmol) in dry DMF (5 mL), sodium hydride (NaH) (0.02 mg, 0.8 mmol) was added and the resulting mixture was stirred for 15 min. After this time 2-amino-3-bromo-5-(4-methoxyphenyl) pyrazine 17a (0.15 g, 0.54 mmol) was added and the resulting mixture was heated at 110° C. for 5 h. The solution was concentrated under reduced pressure and the crude was diluted with Ethyl Acetate and washed with water. Then the organic layer was anidrified over Na$_2$SO$_4$, filtered and the solvent removed under reduced pressure to get a crude that was purified by Al$_2$O$_3$ chromatography using dichloromethane-EtOAc (9:1 v/v) to get 0.13 g of title compound 18e as a brown solid (mp 107-110° C., yield 74%). $^1$H-NMR (CDCl$_3$): 2.36 (s, 3H), 3.80 (s, 3H), 5.03 (s, 2H), 6.89 (d, J=8.8, 2H), 7.17 (d, J=8.2, 2H), 7.40 (d, J=8.3, 2H), 7.70 (d, J=8.8, 2H), 8.25 (s, 1H). MS (ESI): m/z 324 (M+H$^-$).

2-Amino-5-(4-methoxyphenyl)-3-(4-methoxyphenyl)thiopyrazine (18f)

To a solution of 4-methoxylphenylthiol (0.04 mL, 0.36 mmol) in dry DMF (5 mL), sodium hydride (NaH) (0.01 mg, 0.54 mmol) was added the resulting mixture was stirred for 15 min. After this time 2-amino-3-bromo-5-(4-methoxyphenyl)pyrazine 17a (0.10 g, 0.36 mmol) was added and the resulting mixture was heated at 110° C. for 6 h. The solution was concentrated under reduced pressure and the crude was diluted with Ethyl Acetate and washed with water. Then the organic layer was anidrified over Na$_2$SO$_4$, filtered and the solvent removed under reduced pressure to get a crude that was purified by Al$_2$O$_3$ chromatography using dichloromethane-EtOAc (9:1 v/v) to get 0.09 g of title compound 18f as a brown solid (mp 149-151° C., yield 74%). $^1$H-NMR (CDCl$_3$): 3.81 (s, 3H), 3.83 (s, 3H), 4.79 (br s, 2H), 6.86-6.95 (m, 4H), 7.49 (d, J=8.7, 2H), 7.66 (d, J=8.7, 2H), 8.21 (s, 1H). MS (ESI): m/z 340 (M+H$^+$).

2-Amino-5-(4-methoxyphenyl)-3-methylthiopyrazine (18g)

A solution of sodium methylthiolate (0.04 g, 0.54 mmol) in dry DMF (10 mL), was cooled at −10° C. and 2-amino-3-bromo-5-(4-methoxyphenyl)pyrazine 17a (0.10 g, 0.36 mmol) was added and the resulting mixture was stirred at −10° C. for 30 min. The solution was diluted with Ethyl Acetate and washed with brine. Then the organic layer was anidrified over Na$_2$SO$_4$, filtered and the solvent removed under reduced pressure to get a crude that was purified by flash-chromatography using dichloromethane-EtOAc (9:1 v/v) to get 0.07 g of title compound 18g as a white solid (mp 139-140° C., yield 79%). $^1$H-NMR (CDCl$_3$): 2.69 (s, 3H), 3.84 (s, 3H), 4.62 (br s, 2H), 6.96 (d, J=8.8, 2H), 7.82 (d, J=8.8, 2H), 8.12 (s, 1H). MS (ESI): m/z 248 (M+H$^-$).

2-Amino-5-phenyl- 3-(4-methylphenyl)thiopyrazine (18i)

To a solution of 4-methylphenylthiol (0.10 g, 0.80 mmol) in dry acetonitrile (8 mL), sodium hydride (NaH) (0.02 mg, 0.8 mmol) was added and the resulting mixture was stirred for 15 min. After this time 2-amino-3-bromo-5-phenylpyrazine 17b (0.10 g, 0.40 mmol) was added and the resulting mixture was refluxed for 3 h. The solution was quenched with water and taken in Ethyl Acetate. Then the organic layer was anidrified over Na$_2$SO$_4$, filtered and the solvent removed under reduced pressure to get a crude that was purified by Al$_2$O$_3$ chromatography using dichloromethane as eluent, to get 0.08 g of title compound 18i as an orange solid (mp 120-122° C., yield 68%). $^1$H-NMR (CDCl$_3$): 2.33 (s, 3H), 5.17 (br s, 2H), 7.15 (d, J=7.4, 2H), 7.23-7.37 (m, 5H), 7.69 (d, J=7.6, 2H), 8.25 (s, 1H). MS (ESI): m/z 294 (M+H$^+$).

2-Amino-5-phenyl-3-(4-methoxyphenyl)thiopyrazine (18j)

To a solution of 4-methoxyphenylthiol (0.10 mL, 0.80 mmol) in dry acetonitrile (8 mL), sodium hydride (NaH) (0.02 mg, 0.8 mmol) was added the resulting mixture was stirred for 15 min. After this time 2-amino-3-bromo-5-phenylpyrazine 17b (0.10 g, 0.40 mmol) was added and the resulting mixture was refluxed for 3 h. The solution was quenched with water and diluted with Ethyl Acetate. Then the organic layer was anidrified over Na$_2$SO$_4$, filtered and the solvent removed under reduced pressure to get a crude that was purified by flash-chromatography using dichloromethane-ethyl acetate (9:1 v/v) as eluent, to get 0.11 g of title compound 18j as a pale yellow solid (mp 116-118° C., yield 89%). $^1$H-NMR (CDCl$_3$): 3.82 (s, 3H), 4.98 (br s, 2H), 6.93 (d, J=8.7, 2H), 7.27-7.39 (m, 3H), 7.49 (d, J=8.4, 2H), 7.72 (d, J=7.1, 2H) 8.28 (s, 1H). MS (ESI): m/z 310 (M+H$^+$).

2-Amino-5-phenyl-3-(3,5-bis-trifluoromethylphenyl)thiopyrazine (18k)

To a solution of 3,5-bis-trifluoromethylphenylthiol (0.03 mL, 0.20 mmol) in dry DMF (5 mL), sodium hydride (NaH) (0.01 g, 0.42 mmol) was added the resulting mixture was stirred for 15 min. After this time 2-amino-3-bromo-5-phenylpyrazine 17b (0.05 g, 0.20 mmol) was added and the resulting mixture was heated at 110° C. for 1 h. The solution was concentrated under reduced pressure, taken in Ethyl Acetate and washed with water. Then the organic layer was anidrified over Na$_2$SO$_4$, filtered and the solvent removed under reduced pressure to get a crude that was purified by Al$_2$O$_3$ chromatography using dichloromethane as eluent, to get 10 mg of title compound 18k as a pale yellow solid (yield 10%). $^1$H-NMR (CDCl$_3$): 5.10 (br s, 2H), 7.33-7.46 (m, 3H), 7.68-7.72 (m, 2H), 7.87 (s, 1H), 8.05 (s, 2H), 8.37 (s, 1H). MS (ESI): m/z 414 (M−H$^1$).

2-Amino-5-phenyl-3-(4-chlorophenyl)thiopyrazine (18l)

To a solution of 4-chlorophenylthiol (0.20 g, 1.14 mmol) in dry Acetonitrile (30 mL), sodium hydride (NaH) (27 mg, 1.14 mmol) was added and the resulting mixture was stirred for 15 min. After this time 2-amino-3-bromo-5-phenylpyrazine 17b (0.18 g, 0.70 mmol) was added and the mixture refluxed for 17 h. The mixture was then cooled to room temperature, diluted with Ethyl Acetate and washed with water. Then the organic layer was anidrified over Na$_2$SO$_4$, filtered and the solvent removed under reduced pressure to get a crude that was purified by flash chromatography using petroleum ether-EtOAc (7:3 v/v) to get 0.17 g of title compound 18l as a white solid (mp 158-160° C., yield 80%). $^1$H-NMR (CDCl$_3$): 4.90 (br s, 2H), 7.32-7.46 (m, 7H), 7.72-7.75 (m, 2H), 8.34 (s, 1H). MS (ESI): m/z 314 (M+H$^+$).

2-Amino-5-phenyl-3-(4-fluorophenyl)thiopyrazine (18m)

To a solution of 4-fluorophenylthiol (0.26 mL, 2.47 mmol) in dry Acetonitrile (30 mL), sodium hydride (NaH) (60 mg, 2.47 mmol) was added the resulting mixture was stirring for 15 min. After this time 2-amino-3-bromo-5-phenylpyrazine 17b (0.16 g, 0.6 mmol) was added and the mixture refluxed for 2 h. The mixture was then cooled to room temperature, diluted with Ethyl Acetate and washed with water. Then the organic layer was anidrified over Na$_2$SO$_4$, filtered and the solvent removed under reduced pressure to get a crude that was purified by flash chromatography using petroleum ether-EtOAc (7:3 v/v) to get 0.11 g of title compound 18m as a white solid (mp 161-164° C., yield 60%). $^1$H-NMR (CDCl$_3$):

5.00 (br s, 2H), 7.08-7.12 (m, 2H), 7.28-7.38 (m, 3H), 7.52-7.55 (m, 2H), 7.70-7.72 (m, 2H), 8.31 (s, 1H). MS (ESI): m/z 298 (M+H$^+$).

2-Amino-5-phenyl-3-cyclopentylthiopyrazine (18n)

To a solution of cyclopentanethiol (0.18 g, 1.80 mmol) in dry acetonitrile (20 mL), sodium hydride (NaH) (0.04 g, 1.80 mmol) was added the resulting mixture was stirred for 15 min. After this time 2-amino-3-bromo-5-phenylpyrazine 17b (0.15 g, 0.6 mmol) was added and the mixture heated at 80° C. for 2 h, cooled and quenched with water. Then EtOAc was added and the organic layer was anidrified over Na$_2$SO$_4$, filtered and the solvent removed under reduced pressure to get a crude that was purified by flash chromatography using dichloromethane-EtOAc (9:1 v/v) as eluent, to obtain 0.11 g of the title compound 18n as a yellow solid (mp 92-94° C., 67% yield). $^1$H-NMR (CDCl$_3$): 1.68-1.83 (m, 6H), 2.28-2.31 (m, 2H), 4.21-4.28 (m, 1H), 4.93 (br s, 2H), 7.32-7.35 (m, 1H), 7.41-7.45 (m, 2H), 7.91-7.93 (m, 2H), 8.20 (s, 1H). MS (ESI): m/z 272 (Mile).

2-Amino-5-phenyl-3-adamantylthiopyrazine (18o)

To a solution of 1-adamantanethiol (0.07 g, 0.4 mmol) in dry acetonitrile (10 mL), sodium hydride (NaH) (9 mg, 0.4 mmol) was added and the resulting mixture was stirred for 15 min. After this time 2-amino-3-bromo-5-phenylpyrazine 17b (0.05 g, 0.2 mmol) was added and the mixture heated at 80° C. for 4 h, cooled and quenched with water. Then EtOAc was added and the organic layer was anidrified over Na$_2$SO$_4$, filtered and the solvent removed under reduced pressure to get a crude that was purified by flash chromatography using petroleum ether-EtOAc (7:3 v/v) as eluent, to obtain 0.04 g of the title compound 18o as a yellow oil (62% yield). $^1$H-NMR (CDCl$_3$): 1.73 (s, 6H), 2.08 (s, 3H), 2.23 (s, 6H), 5.13 (br s, 2H), 7.32-7.36 (m, 1H), 7.42-7.46 (m, 2H), 7.91-7.93 (m, 2H), 8.29 (s, 1H). MS (ESI): m/z 338 (M+H$^+$).

2-Amino-3-(benzo[d]thiazol-2-ylthio)-5-phenylpyrazine (18p)

To a solution of 2-mercaptobenzothiazol (0.07 g, 0.4 mmol) in dry DMF (7 mL), sodium hydride (NaH) (9 mg, 0.4 mmol) was added and the resulting mixture was stirred for 15 min. After this time 2-amino-3-bromo-5-phenylpyrazine 17b (0.05 g, 0.2 mmol) was added and the mixture heated at 110° C. for 4 h. The solvent was removed under reduced pressure and the crude was diluted with dichloromethane, washed with water. Then the organic layer was anidrified over Na$_2$SO$_4$, filtered and the solvent removed under reduced pressure to get a crude that was purified by flash chromatography using dichloromethane-EtOAc (9:1 v/v) to get 15 mg of title compound 18p as a pale yellow solid (yield 23%). $^1$H-NMR (CDCl$_3$): 5.36 (br s, 2H), 7.28-7.47 (m, 6H), 7.59-7.76 (m, 1H), 7.91-7.93 (m, 2H), 8.53 (s, 1H). MS (ESI): m/z 359 (M+Na$^1$).

2-Amino-5-phenyl-3-phenoxypyrazine (18q)

To a cooled solution of phenol (0.07 mL, 0.80 mmol) in dry DMF (5 mL), sodium hydride (NaH) (0.02 g, 0.80 mmol) was added and the resulting mixture was cooled at 5-10° C. and stirred for 15 min. After this time 2-amino-3-bromo-5-phenylpyrazine 17b (0.25 g, 1.00 mmol) was added and the mixture refluxed for 20 h, cooled and extracted with EtOAc. The organic layer was washed with water, anidrified over Na$_2$SO$_4$, filtered and the solvent removed under reduced pressure to get a crude that was purified by flash chromatography using dichloromethane-EtOAc (70:30 v/v) as eluent, to obtain 0.13 g of the title compound 18q as a pink solid (mp 129-131° C., 62% yield). $^1$H-NMR (CDCh): 5.04 (br s, 2H), 7.28-7.43 (m, 8H), 7.69-7.73 (m, 2H), 8.18 (s, 1H). MS (ESI): m/z 264 (M+H$^+$).

2-Amino-5-phenyl-3-(4-hydroxyphenyl)pyrazine (18r)

To a cooled (−10° C.) solution of 18j (0.17 g, 0.55 mmol) in dichloromethane (15 mL), a 1.0 M sol. in CH$_2$Cl$_2$ of BBr$_3$ (2.75 mL, 2.75 mmol) was added. The resulting mixture was stirred for 3 h at room temperature. Then the solution was washed with NaHCO$_3$s.s., the organic layer was dried over sodium sulphate, filtered and concentrated under reduced pressure to get a crude that was purified by flash chromatography using dichloromethane-EtOAc (9:1 v/v) as eluent, to obtain 0.13 g of the title compound 18r as a yellow solid (mp 181-183° C., yield 80%). $^1$H-NMR (CD$_3$OD): 4.82 (s, 2H), 6.85 (d, J=8.4, 2H), 7.16-7.26 (m, 3H), 7.37 (d, J=8.8, 2H), 7.62 (d, J=8.4, 2H), 8.14 (s, 1H). MS (ESI): m/z 296 (M+H$^+$).

2-Amino-5-phenyl-3-phenylsulphynylpyrazine (19)

To a solution of 2-amino-5-phenyl-3-phenylthiopyrazine 18b (0.06 mg, 0.21 mmol) in methanol (5 mL), Oxone™ (0.40 g, 0.65 mmol) was added at 0° C. dropwisc, in water (3 mL). The reaction mixture was stirred at room temperature for 3 h, extracted with dichloromethane and washed with NaCl sat. The organic layer was dried over Na$_2$SO$_4$, filtered and the solvent removed under reduced pressure to get a crude that was purified by flash chromatography (dichloromethane, EtOAc 80:20) to obtain 0.01 g of the title compound 19 as an orange solid (mp 137-140° C., 29% yield). $^1$H-NMR (CDCl$_3$): 6.13 (br s, 2H), 7.34-7.53 (m, 6H), 7.76-7.88 (m, 4H), 8.45 (s, 1H). MS (ESI): m/z 318 (M+Na$^1$).

General Procedures for the Synthesis of Compounds 20a-e.

To a Schlenk's tube containing pyridine hydrochloride (5 mmol) heated at 120° C., compound 14a (or 18a,c-e) (0.25 mmol) was added. The resulting mixture was stirred at 190° C. under argon atmosphere for 1.5-2 h. Then the mixture was cooled at room temperature, diluted with ethyl acetate and washed with NaHCO$_3$ sat. The organic layer was dried over Na$_2$SO$_4$, filtered and the solvent removed under reduced pressure to get a crude that was purified by flash chromatography (eluent reported in the compound description) to obtain compounds 20a-e.

2-Amino-3-benzyl-5-(4-hydroxyphenyl)pyrazine (20a)

Title compound was purified by flash chromatography using a mixture of dichloromethane-EtOAc (1:1 v/v) as eluent, to get 0.09 g of the compound 20a as a pale brown solid (mp 214-215° C., 68% yield). $^1$H-NMR (CDCl$_3$): 4.17 (s, 2H), 4.47 (br s, 2H), 6.91 (d, J=8.7, 2H), 7.26-7.31 (m, 5H), 7.81 (d, J=8.5, 2H), 8.28 (s, 1H). MS (ESI):m/z 278 (M+H$^+$).

2-Amino-3-thiophenyl-5-(4-hydroxyphenyl)pyrazine (20b)

Title compound was purified by flash chromatography using a mixture of dichloromethane-EtOAc (1:1 v/v) as eluent, to get 0.05 g of the compound 20b as an orange oil (58% yield). ¹H-NMR (CD₃OD): 6.71 (d, J=8.6, 2H), 7.36-7.41 (m, 3H), 7.47-7.54 (m, 4H), 8.15 (s, 1H). MS (ESI):m/z 294 (M+H⁺).

2-Amino-3-(4-chloro)phenylthio-5-(4-hydroxyphenyl)pyrazine (20c)

Title compound was purified by Al₂O₃ chromatography using a mixture of EtOAc-MeOH (9:1 v/v) as eluent, to get 0.10 g of the compound 20c as an brown solid (mp 133-134° C., 52% yield). ¹H-NMR (CDCl₃): 4.90 (br s, 2H), 6.87 (d, J=8.8, 2H), 7.38 (d, J=8.6, 2H), 7.46 (d, J=8.6, 2H), 7.66 (d, J=8.7, 2H), 8.30 (s, 1H). MS (ESI):m/z 328 (M–H⁺).

2-Amino-3-(3,5-bis-trifluoromethyl)phenylthio-5-(4-hydroxyphenyl)pyrazine (20d)

Title compound was purified by Al₂O₃ chromatography using a mixture of EtOAc-MeOH (9:1 v/v) as eluent, to get 0.03 g of the compound 20d as an pale yellow solid (28% yield). ¹H-NMR (CD₃OD): 4.86 (br s, 2H), 6.83 (d, J=8.7, 2H), 7.61 (d, J=8.7, 2H), 7.85 (s, 1H), 8.03 (s, 2H), 8.32 (s, 1H). MS (ESI):m/z 432 (M+H¹).

2-Amino-3-(4-methyl)phenylthio-5-(4-hydroxyphenyl)pyrazine (20e)

Title compound was purified by flash chromatography using a mixture of EtOAc as eluent, to get 0.05 g of the compound 20e as an yellow solid (30% yield). ¹H-NMR (CD₃OD): 2.36 (s, 3H), 4.85 (s, 2H), 5.67 (br s, 1H), 6.82 (d, J=8.8, 2H), 7.18 (d, J=8.0, 2H), 7.39 (d, J=8.0, 2H), 7.64 (d, J=8.8, 2H), 8.24 (s, 1H). MS (ESI):m/z 310 (M+H⁺).

1,1-Diethoxy-3-phenyl-propan-2-one (22)

To a mixture of ethyl ethoxyacetate (2.50 mL, 14.00 mmol) in anhydrous THF (20 mL) the Grignard salt 21 (1M in diethylether) (20.00 mL, 20.00 mmol) was added dropwise at –78° C. The mixture was stirred at –78° C. for 2 h, then 20% NH₄Cl aq was added and extracted with EtOAc. The collected organic layers were dried over Na₂SO₄, filtered and the solvent removed under reduced pressure to get a crude that was purified by flash chromatography (petroleum ether, EtOAc 90:10) to obtain 2.60 g of the title compound 22 as a colorless oil (84% yield). ¹H-NMR (CDCl₃): 1.16-1.23 (m, 6H), 3.39-3.77 (m, 4H), 3.84 (s, 2H), 4.58 (s, 1H), 7.15-7.30 (m, 5H). MS (ESI): m/z 245 (M+Na).

General Procedure for the Synthesis of Compounds 23a-r.

A mixture of the pyrazine derivative 14a-e, 18a-r, 19,20a-e (0.20 mmol), phenyldiethoxyacetone 22 (0.11 g, 0.48 mmol) and conc. HCl (0.13 mL) in ethanol (25 mL) was refluxed for 4-8 h. The solvent was removed in vacuo and the crude recovered with CH₂Cl₂ and washed with water. The organic layer was dried over Na₂SO₄, filtered and the solvent removed under reduced pressure. The purification of the crude was performed by flash chromatography eluting with the suitable solvent to afford the expected compound 23a-r.

2,8-Dibenzyl-6-(4-hydroxyphenyl)imidazo[1,2-a]pyrazin-3(7H)-one (23a)

The purification by flash chromatography was performed with dichloromethane-MeOH (95:5 v/v) to get 0.04 g of the title compound 23a as a brown oil (28% yield). ¹H-NMR (CD₃OD): 4.14 (s, 2H), 4.35 (s, 2H), 6.80-6.85 (m, 2H), 7.12-7.42 (m, 12H), 7.52 (s, 1H). MS (ESI): m/z 406 (M–H).

2,8-Dibenzyl-6-phenylimidazo-[1,2-a]pyrazin-3(7H)-one (23b)

The purification by flash chromatography was performed with EtOAc to get 0.048 g of the title compound 23b as an orange oil (29% yield). ¹H-NMR (CDCl₃): 4.16 (s, 2H), 4.34 (s, 2H), 7.15-7.33 (m, 16H). MS (ESI): m/z 392 (M+H⁺).

Figure 5:
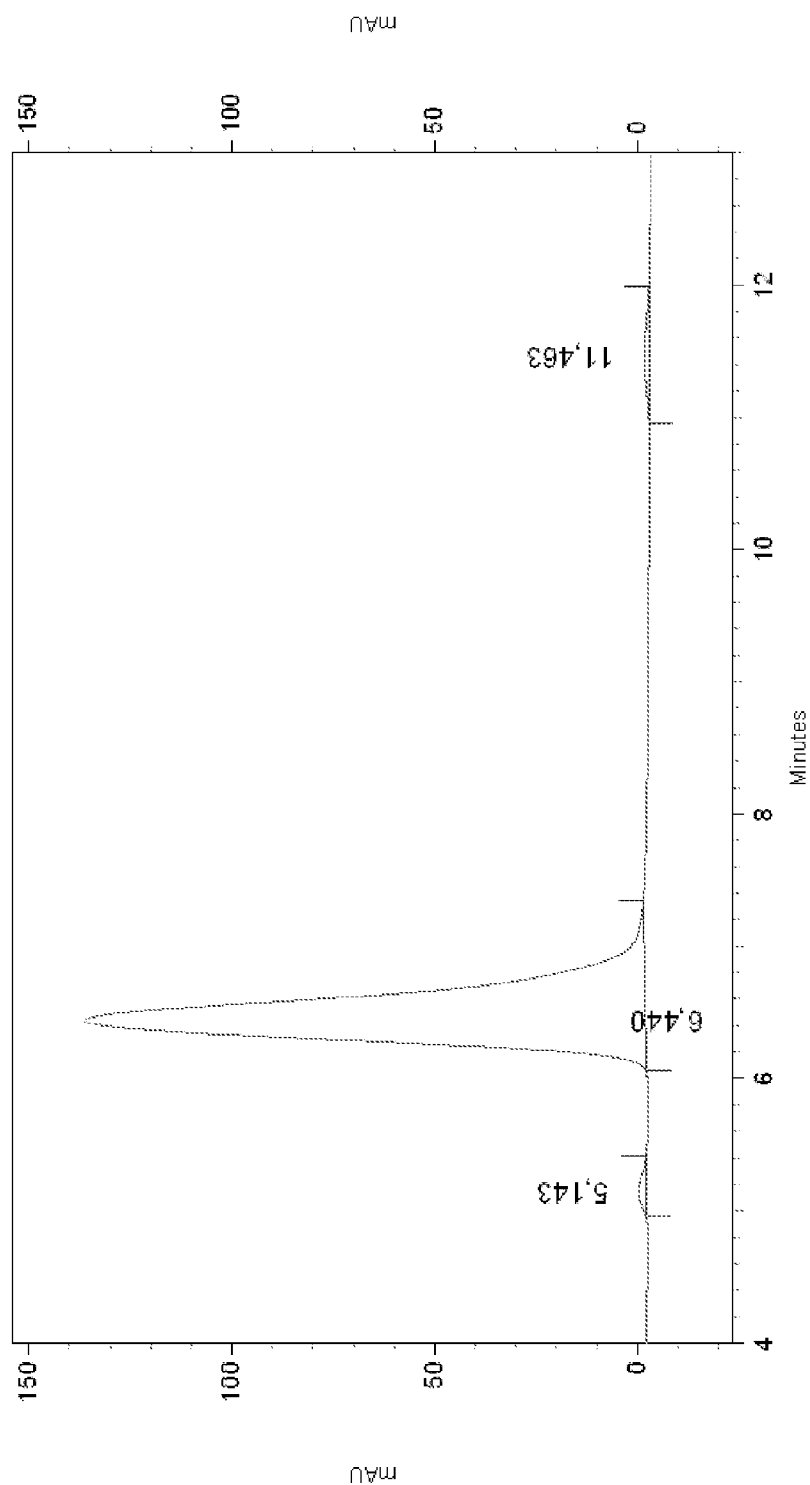
FIG. 5: HPLC analysis of compound 23b using as operative conditions: MOBILE PHASE 0.1% trifluoroacetic acid (TFA) in water and 0.1% TFA in $CH_3CN$ (50:50). Mobile phase flux 0.7 ml/min, Absorbance 260 nm. Peak parameters are shown in Table 7 below.

HPLC analysis of compound 23b using as operative conditions: MOBILE PHASE 0.1% trifluoroacetic acid (TFA) in water and 0.1% TFA in CH₃CN (50:50). Mobile phase flux 0.7 ml/min. Absorbance 260 nm is shown in FIG. 5 and relative Table 7. The compound 23b used in bio-chemiluminescence experiments showed 98% purity as can be seen from the peak area of peak 2 with a retention time of 6.44 min.

TABLE 7

HPLC analysis of compound 23b

| Pk # | Area | Area Percent | Height | Height Percent | Retention Time (min) |
|---|---|---|---|---|---|
| 1 | 108928 | 0.856 | 7351 | 1.304 | 5.143 |
| 2 | 12481792 | 98.080 | 552456 | 97.971 | 6.440 |
| 3 | 135383 | 1.064 | 4091 | 0.725 | 11.463 |
| Totals | 12726103 | 100.000 | 563898 | 100.000 | |

6-(4-Aminophenyl)-2,8-dibenzylimidazo[1,2-a]pyrazin-3(7H)-one (23c)

The purification by flash chromatography was performed with chloroform-MeOH (9:1 v/v) to get 0.03 g of the title compound 23c as a pale brown solid (24% yield). ¹H-NMR (CD₃OD): 4.15 (s, 2H), 4.38 (s, 2H), 6.74 (d, J=8.5, 2H), 7.20-7.35 (m, 12H), 7.53 (s, 1H). MS (ESI): m/z 407 (M+H¹).

2,8-Dibenzyl-6-(4-methoxyphenyl)imidazo-[1,2-a]pirazin-3(7H)-one (23d)

The purification by flash chromatography was performed with dichloromethane-EtOAc (70:30) to get 0.009 g of the title compound 23d as a yellow oil (25% yield). ¹H-NMR (CDCl₃): 3.71 (s, 3H), 4.14 (s, 2H), 4.34 (s, 2H), 6.72 (d, J=9.0, 2H), 7.15-7.36 (m, 13H). MS (ESI): m/z 422 (M+H⁺).

2,8-Dibenzyl-6-[3,4-(methylendioxy)-phenyl]imidazo-[1,2-a]pirazin-3(7H)-one (23e)

The solid obtained by precipitation from EtOAc was filtered off, washed with n-hexane and diethyl ether and dried in vacuum to obtain 0.040 g of the title compound 23e as a yellow solid (mp 216-218° C., 48% yield). ¹H-NMR (CH₃OD): 4.26 (s, 2H), 4.50 (s, 2H), 6.02 (s, 2H), 6.93 (d, J=7.8, 1H), 7.23-7.43 (m, 12H), 8.47 (s, 1H). MS (ESI, negative ions): m/z 434 (M–H¹).

2-Benzyl-6-phenyl-8-(phenylthio)imidazo-[1,2-a]pirazin-3(7H)-one (23f)

The solid obtained by precipitation from a mixture of dichloromethane and EtOAc was filtered off and dried under vacuum to obtain 0.010 g of the title compound 23f (mp 205-207° C., 14% yield). ¹H-NMR (CH₃OD): 4.31 (s, 2H), 7.32-7.37 (m, 8H), 7.57-7.60 (m, 3H), 7.71-7.75 (m, 4H), 8.61 (s, 1H). MS (ESI): m/z 410 (M+H$^+$).

2-Benzyl-6-(4-hydroxyphenyl)-8-(phenylthio)imidazo[1,2-a]pyrazin-3(7H)-one (23g)

The purification by flash chromatography was performed with dichloromethane-MeOH (9:1 v/v) to get 0.07 g of the title compound 23g as a pale brown oil (30% yield). $^1$H-NMR (CD$_3$OD): 4.13 (s, 2H), 6.70 (d, J=8.6, 2H), 7.18-7.29 (m, 5H), 7.49-7.53 (m, 5H), 7.65-7.67 (m, 2H), 8.15 (s, 1H). MS (ESI): m/z 426 (M+H$^+$).

2-Benzyl-8-(4-chlorophenylthio)-6-(4-hydroxyphenyl)imidazo[1,2-a]pyrazin-3(7H)-one (23i)

The purification by flash chromatography was performed with dichloromethane-MeOH (95:5 v/v) to get 0.012 g of the title compound 23i as a pale brown oil (10% yield). $^1$H-NMR (CD$_3$OD): 4.18 (s, 2H), 6.76-6.78 (m, 2H), 7.17-7.31 (m, 5H), 7.51-7.58 (m, 4H), 7.66-7.68 (m, 2H), 8.18 (s, 1H). MS (ESI): m/z 458 (M–H$^+$).

2-Benzyl-6-(4-hydroxyphenyl)-8-(p-tolylthio)imidazol[1,2-a]pyrazin-3(7H)-one (23j)

The purification by flash chromatography was performed with dichloromethane-MeOH (9:1 v/v) to get 0.015 g of the title compound 23j as an orange oil (20% yield). $^1$H-NMR (CD$_3$OD): 2.43 (s, 3H), 4.14 (s, 2H), 6.71 (d, J=8.8, 2H), 7.26-7.32 (m, 7H), 7.50-7.53 (m, 4H), 8.17 (s, 1H). MS (ESI): m/z 440 (M–H$^1$).

2-Benzyl-6-phenyl-8-(p-tolylthio)imidazo[1,2-a]pyrazin-3(7H)-one (23k)

The purification by flash chromatography was performed with dichloromethane-MeOH (95:5 v/v) to get 0.05 g of the title compound 23k as an orange oil (20% yield). $^1$H-NMR (CDCl$_3$): 2.37 (s, 3H), 4.03 (s, 2H), 6.86-6.93 (m, 3H), 7.11 (d, J=7.2, 2H), 7.17 (d, J=8.4, 2H), 7.24-7.28 (m, 3H), 7.38 (d, J=7.6, 2H), 7.48-7.50 (m, 2H), 8.06 (s, 1'-1). MS (ESI): m/z 424 (M+H$^+$).

2-Benzyl-8-(4-methoxyphenylthio)-6-phenylimidazo[1,2-a]pyrazin-3(7H)-one (23l)

The purification by flash chromatography was performed with dichloromethane-MeOH (95:5 v/v) to get 0.20 g of the title compound 23l as an orange oil (36% yield). $^1$H-NMR (CDCl$_3$): 3.80 (s, 3H), 4.02 (s, 2H), 6.84-6.91 (m, 5H), 7.03 (d, J=6.8, 2H), 7.23-7.26 (m, 3H), 7.39 (d, J=8.8, 2H), 7.50-7.52 (m, 2H), 8.08 (s, 1H). MS (ESI): m/z 440 (M+H$^+$).

2-Benzyl-8-(4-hydroxyphenylthio)-6-phenylimidazo[1,2-a]pyrazin-3(7H)-one (23m)

The purification by flash chromatography was performed with dichloromethane-MeOH (95:5 v/v) to get 0.06 g of the title compound 23m as an orange oil (32% yield). $^1$H-NMR (CD$_3$)$_2$CO: 4.11 (s, 2H), 6.98 (d, J=8.4, 2H), 7.22-7.33 (m, 8H), 7.48-7.51 (m, 2H), 7.80 (d, J=7.6, 2H), 8.28 (s, 1H). MS (ESI): m/z 426 (M+H$^+$).

2-Benzyl-8-(4-chlorophenylthio)-6-phenylimidazo[1,2-a]pyrazin-3(7H)-one (23n)

The purification by flash chromatography was performed with dichloromethane-MeOH (95:5 v/v) to get 0.03 g of the title compound 23n as an orange oil (16% yield). $^1$H-NMR (CDCl$_3$): 4.00 (s, 2H), 6.81-6.90 (m, 3H), 6.97 (d, J=6.8, 2H), 7.27-7.35 (m, 7H), 7.50-7.53 (m, 2H), 8.13 (s, 1H). MS (ESI): m/z 444 (M+H$^+$).

2-Benzyl-6-phenyl-8-(4-fluorophenylthio)imidazo-[1,2-a]pirazin-3(7H)-one (23o)

The purification by flash chromatography was performed with dichloromethane-MeOH (95:5) to get 0.04 g of the title compound 23o as a yellow oil (20% yield). $^1$H-NMR (CDCl$_3$): 4.02 (s, 2H), 6.83-6.91 (m, 3H), 7.00-7.07 (m, 4H), 7.26-7.28 (m, 3H), 7.40-7.43 (m, 2H), 7.49-7.52 (m, 2H), 8.13 (s, 1H). MS (ESI): m/z 428 (M+H$^+$).

2-Benzyl-6-phenyl-8-(ciclopentylthio)imidazo-[1,2-a]pirazin-3(7H)-one (23p)

The purification by flash chromatography was performed with dichloromethane-MeOH (95:5) to get 0.1 g of the title compound 23p as a yellow solid (mp 220-222° C., 35% yield). $^1$H-NMR (CDCl$_3$): 1.42-1.53 (m, 6H), 2.09-2.13 (m, 2H), 3.92 (s, 2H), 4.17-4.20 (m, 1H), 6.78-6.70 (m, 3H), 6.91-6.93 (m, 2H), 7.31-7.40 (m, 3H), 7.80-7.82 (m, 2H), 8.12 (s, 1H), 10.20 (br s, 1H). MS (ESI): m/z 402 (M+H$^1$).

2-Benzyl-6-phenyl-8-(adamantylthio)imidazo-[1,2-a]pirazin-3(7H)-one (23q)

The purification by flash chromatography was performed with dichloromethane-MeOH (95:5) to get 0.06 g of the title compound 23q as a yellow oil (25% yield). $^1$H-NMR (CDCl$_3$): 1.66 (s, 6H), 1.98 (s, 3H), 2.17 (s, 6H), 3.97 (s, 2H), 6.82-6.88 (m, 3H), 6.98-7.00 (m, 2H), 7.31-7.40 (m, 3H), 7.81 (d, J=7.2, 2H), 8.07 (s, 1H). MS (ESI): m/z 466 (M–H$^+$).

2-Benzyl-6-phenyl-8-phenoxyimidazo-[1,2-a]pirazin-3(7H)-one (23r)

The purification by flash chromatography was performed with dichloromethane-MeOH (95:5) to get 0.02 g of the title compound 23r as a red oil (10% yield). $^1$H-NMR (CD$_3$OD): 4.23 (s, 2H), 7.14-7.46 (m, 11H), 7.61-7.67 (m, 4H), 8.27 (s, 1H). MS (ESI): m/z 394 (M+H$^+$).

2-Benzyl-8-(4-methoxyphenylthio)-6-phenylimidazo[1,2-a]pyrazin-3-yl acetate (25a)

To a solution of 23l (25 mg, 0.06 mmol) in 4 mL of dichloromethane, acetyl chloride (8 µL, 0.12 mmol) and 4-(dimethylamino)pyridine (DMAP) (5 mg, 0.03 mmol) were added, the resulting mixture was stirred at room temperature for 15 min. Then the solution was washed with water and the organic layer was dried over Na$_2$SO$_4$, filtered and the solvent removed under reduced pressure to obtain 18 mg (yield 66%) of 25a as a red oil. $^1$H-NMR (CDCl$_3$): 2.10 (s, 3H), 3.88 (s, 3H), 4.20 (s, 2H), 7.00-7.02 (m, 2H), 7.22-7.33 (m, 8H), 7.61-7.64 (m, 4H), 7.68 (s, 1H). MS (ESI): m/z 482 (M+H$^+$).

Chemiluminescence Spectrums.
Operative Conditions.

The coelenterazine analogues 23b,e,f (1 mg) were dissolved in 5 mL of MeOH to prepare a stock solutions of 0.1-0.3 mg/mL of concentration. Consequently, 10 µL of the stock solution were directly diluted in the quartz cuvette reader of the Fluorescence Spectrophotometer Shimadzu RF5001PC, containing 3 mL of DMSO, to obtain a final sample concentration of 1-3 µg/mL.

Instrument Setting:

| Scan Mode | Emission |
|---|---|
| Ex Wavelenght | 900.00 |
| Em Start W1 | 400.00 |
| Em End W1 | 650.00 |
| No. of repeats | 10 |
| Time Delay (s) | 12 |
| Scan speed | Very fast |
| Excitation Slit | 1.5 |
| Emission Slit | 30.0 |
| Sensitivity | High |
| Resolution | 1.0 |
| Response | 0.25 |

Figure 6:
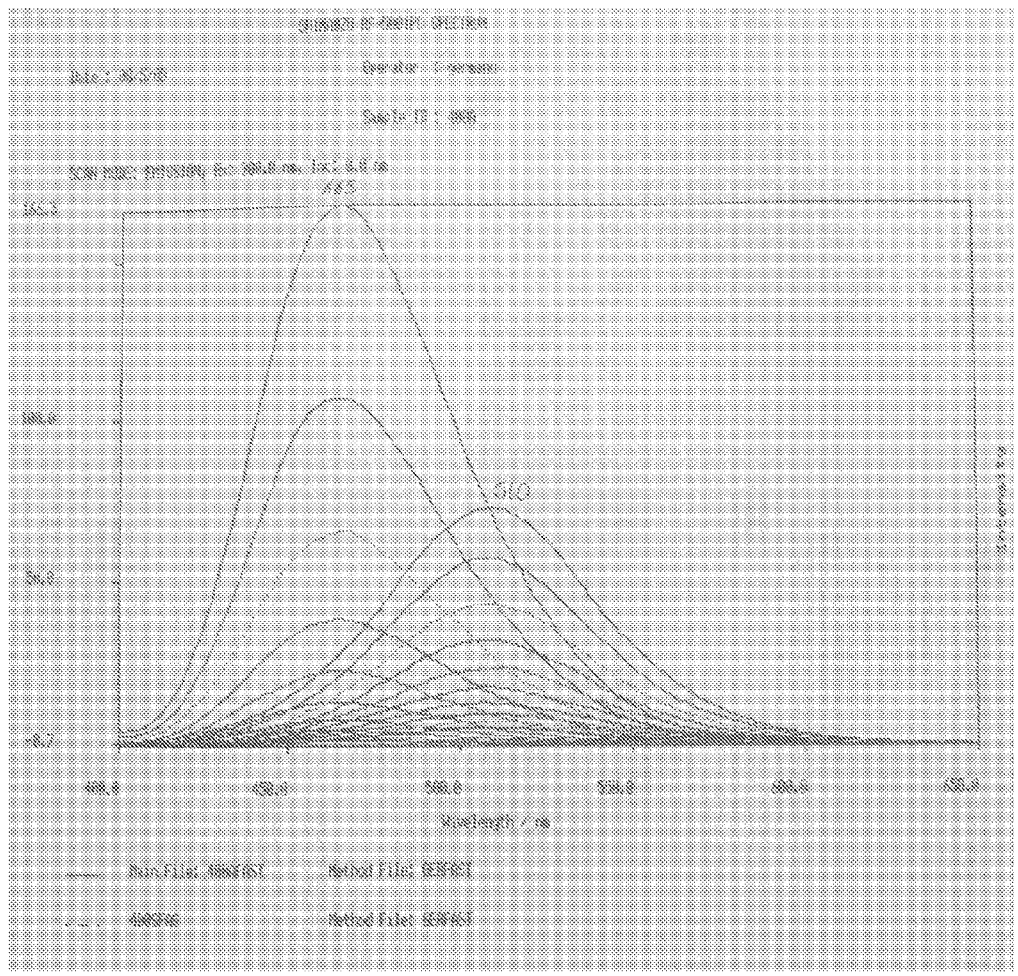
FIG. 6: Chemiluminescent spectrum of 23b (max. emission peak at 465 nm), compared with chemiluminescent spectrum of 23f (max. emission peak at 510 nm).

The chemiluminescent spectrum of 23b (max. emission peak at 465 nm), compared with chemiluminescent spectrum of 23f (max. emission peak at 510 nm) is shown in FIG. 6. The emission shift between spectrums is about 45 nm, the relative lowest intensity of 23f is owing to a minor energy of the emitting intermediate, that correspond to a major wavelength. As expected, the kinetic of chemiluminescence of 23f is slower than 23b.

Bioluminescence Spectrum.

Operative Conditions.

Bioluminescence was measured according to standard procedures.[40]

Figure 7:
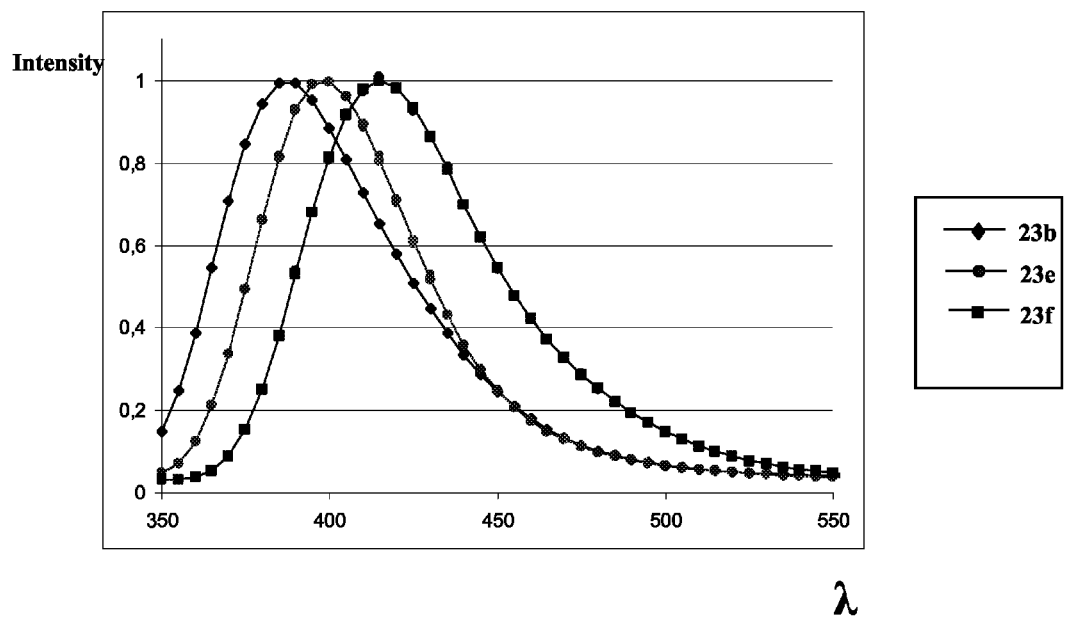
FIG. 7: Bioluminescent spectra (RLuC) with 23b, 23e, 23f.

The bioluminescent spectra (RLuC) with 23b (2-(4-dchydroxy)-coelenterazine as reference compound) 23e, 23f are shown in FIG. 7

Compound 23f displays an emission of about 415 nm, representing a shift of about 30 nm in respect of compound 23b.

Relative peak parameters are presented in Table 8.

TABLE 8

Bioluminescent emission (*Renilla* Luciferase) measured in triplicate (1$^{st}$, 2$^{nd}$ and 3d), of compounds 23b (2-(4-dehydroxy)-coelenterazine as reference compound), 23e, 23f.

| | 1st | 2nd | 3d |
|---|---|---|---|
| | | max | |
| 23b | 387.4 | 392.1 | 393.0 |
| 23e | 397.6 | 397.5 | 398.2 |
| 23f | 415.1 | 419.4 | 424.3 |
| | | Shifts vs.23b | |
| 23e | 10.2 | 5.5 | 5.2 |
| 23f | 27.7 | 27.4 | 31.4 |

Figure 8:
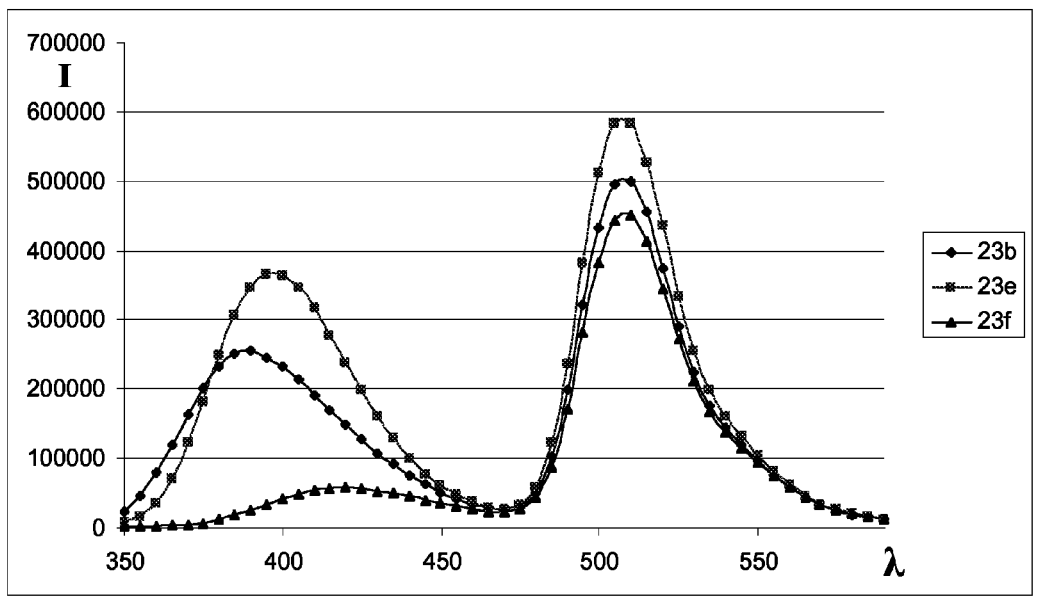
FIG. 8: BRET spectrum beetwen RLuC (donor) and Green Fluorescent Protein GFP (acceptor) with 23b,e,f analogues as substrate.
Figure 9:
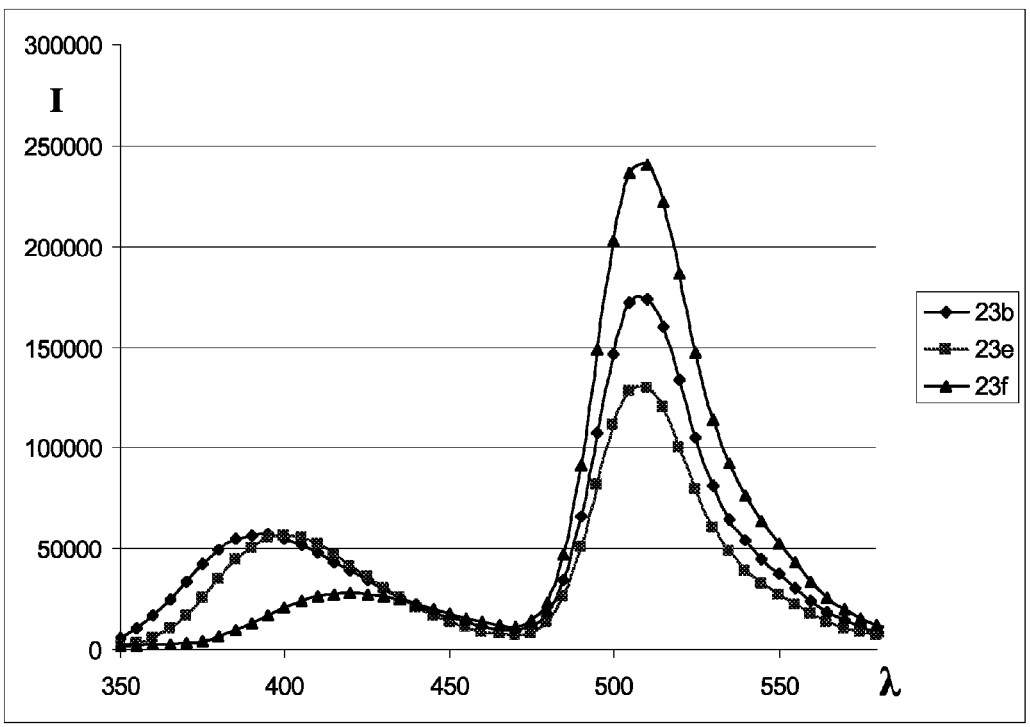
FIG. 9: BRET spectrum beetwen RLuC (donor) and Green Fluorescent Protein GFP (acceptor) with 23b,e,f analogues as substrate.
Figure 10:
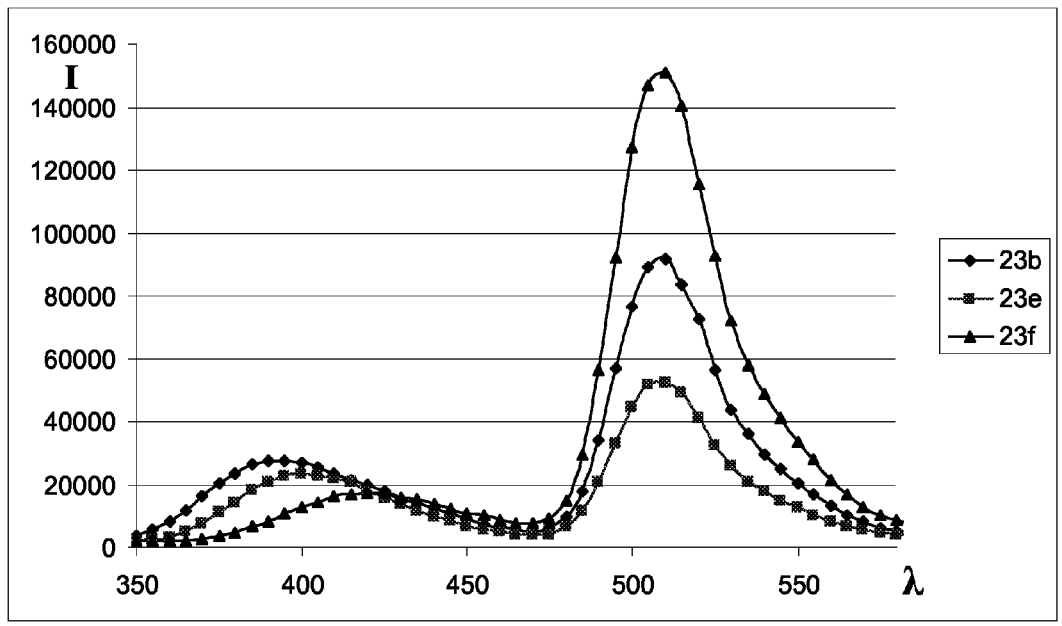
FIG. 10: BRET spectrum beetwen RLuC (donor) and Green Fluorescent Protein GFP (acceptor) with 23b,e,f analogues as substrate.

Time course of BRET experiment carried out at three different times, beetwen RLuC (donor) and Green Fluorescent Protein GFP (acceptor) with 23b,e,f analogues as substrate are shown in FIG. 8-10. While the emission of compounds 23b and 23e decrease over time, the emission of compound 23f is long lasting (see in particular FIG. 10).

The chemiluminescence and bioluminescence of compounds 23i and 23n was also measured and is presented in Table 9 below.

TABLE 9

Chemi-Bioluminescent results relative to compounds 23i, 23n.

| Comp. | Chemil. Imax | Biolum. Imax |
|---|---|---|
| 23i | 505 nm | 510 nm |
| 23n | 505 nm | 470 nm |

These compounds display very interesting bio-chemiluminescent properties with improved red-shifted photoemission.

REFERENCES

1. A. K. Campbell, "Chemiluminescence: Principles and Applications in Biology and Medicine", 1988, VCH, Chichester, England.
2. FLIPR™ Assays to Measure GPCR and Ion Channel Targets http://www.ncgc.nih.gov/guidance/section9.html
3. Fan, F.; Wood, K. V. *Assay Drug Dev. Technol.* 2007, 5, 127-36.
4. Teranishi, K. *Bioorg. Chem.* 2007, 35, 85-111.
5. Auld D. S. et al *J. Med. Chem.* 2008, 51, 2372-2386.
6. Matthews J. C.; Hori H.; Cormier M. J. *Biochemistry* 1977, 16, 5217.
7. (a) *Photomultiplier Tubes: Basics and Applications* (Second Edition), Hamamatsu Photonics, Hamamatsu City, Japan, (1999). (b) Z. Zhang et al *Anal. Chim. Acta* 2005, 541, 37-46.
8. Eglen R. M et al *ASSAY and Drug Development Technologies* 2008, 6, 659-671.
9. Nowycky M. C.; Thomas A. P *J. Cell Science* 2002, 115, 3715-3716.
10. Hart R. C. et al *Biochemistry*, 1979, 18, 2204-2210.
11. Shimomura O, Teranishi K. *Luminescence* 2000, 15, 51-8.
12. (a) Vysotski E. S. et al *Acc. Chem. Res.* 2004, 37, 405-15. (b) Liu Z. J.et al *Proc Natl Acad Sci USA* 2006, 103, 2570-5. (c) Vysotski E. S. et al. *Molecular Biology,* 2006, 40, 355-367.
13. (a) Shimomura, O. et al *Biochem. J.* 1993, 296, 549-551. (b) Inouye S.; Shimomura O. *Biochemical and Biophysical Research Communications* 1997, 233, 349-353. (c) Wu C.; et al. *Tetrahedron Letters* 2001, 42, 2997-3000. (d) S. Inoue, et al., *Chem. Lett* 1975, 141-144. (e) Teranishi, K.; Goto, T. *Bull. Chem. Soc. Jpn.* 2000, 73, 465-469.
14. Bronstein I.; et al., *Anal. Biochem.* 1994, 219, 169-181.
15. (a) Loening A.; Wu A.; Gambhir S. S, *Nature Methods,* 2007, (4), 8, 641-643. (b) Greer L. F.; Szalay A., *Luminescence,* 2002, 17, 43-74
16. (a) Bhaumik S.; Gambhir S. S. *Proc. Natl. Acad. Sci. USA* 2002, 99, 377-382. (b) Tannous B. A.; et al., *Mol. Ther.* 2005, 11, 435-443.
17. Venisnik, K. M. *Protein Eng. Des. Sel.* 2006, 19, 453-460.
18. So M. K.; et al., *Nat. Biotechnol.* 2006, 24, 339-343.
19. (a) Zhao H; et al., *J. Biomed. Opt.* 2005, 10, 41210; (b) Bovolenta S, et al., *J. Biomol. Screen.* 2007, 12, 694.
20. (a) Pfleger K.; Eidne K. *Nature Methods Reviews,* 2006, 3, 165-174. (b) Kroeger K.; Hanyaloglu A. C.; Eidne K. A. *Letters in Peptide Science,* 2002, 8, 155-162.
21. Nakamura, H.; et al. *Tetrahedron Lett.* 1998, 39, 301-304.
22. (a) Tarpey M. M et al., *Circulation Research* 1999, 84, 1203-1211. (b) Lucas M.; Solano F. *Anal Biochem.* 1992, 206, 273-7. (c) Buttke T. M.; Sandstrom P. A. *Immunol Today* 1994, 15, 7. (d) Thomson, C. M.; Herring, P. J.; Campbell, A. K. *J. Biolumin. Chemilumin.* 1997, 12, 87-91. (e) de Wergifosse, B.; et al., *J. Exp. Biol.* 1998, 201, 1211-1221. (f) Dubuisson, M. L. N.; Rees, J. F.; Marchand-Brynaert, *J. Drug Dev. Ind. Pharm.* 2005, 31, 827-849. (g)

de Wergifosse, B.; et al., In *A New Function for Coelenterazine Oxidation Product Supports the Non-Bioluminescent Evolutionary Origin of the Luciferin*, Proceedings of the 10th International Symposium, Bologna, Italy, 1998.

23. (a) Blanquart C.; et al., *Mol. Pharmacol.* 2006, 70, 1802-1811. (b) Xu Y.; et al., *Proc Natl Acad Sci USA* 1999, 96, 151-156.
24. Seth T.; et al., *Anal. Chem.* 2006, 78, 1520-1527.
25. (a) D. E. Jenkins, et al., *Clinical & Experimental Metastasis*, 2003, 20, 733-744. (b) G. Dikmen, et al., Turk *J. Med. Sci*, 2005, 35, 65-70.
26. Isobe, M.; Kuse, M.; Yasuda, Y. *Bioorg. Med. Chem.* 1998, 8, 2919-2924.
27. (a) Jones, K.; et al., *Trends Biotechnol.* 1999, 17, 477-481. (b) Jones, K.; et al., *Synlett* 1996, 509-510.
28. Adamczyk, M et al., *Tetrahedron* 2003, 59, 8129-8142.
29. Nakamura, H.; Takeuchi, D.; Murai, A. *Synlett* 1995, 1227-1228.
30. M. Adamczyk, et al., *Org. PreP. and Proc. Int.* 2001, 33 (5), 477-485.
31. Hirano T.; et al., *Tetrahedron*, 1997, 53, 12903-12916.
32. Nakamura H., Aizawa M., Murai A., *Synlett*, 1996, 1015-1017.
33. (a) Bos R.; et al., *J. Am. Chem. Soc.*, 2009, 131, 2770-2771; (b) Taniguchi M.; et al., *J. Am. Chem. Soc*, 2009, 131, 14146-14147.
34. D. A. De Bie, et al., *Tetrahedron*, 1988, 44, 10, 2977-2983.
35. N. Sato, *J. Heterocyclic Chem.*, 1978, 15, 665-670.
36. M. Shimazaki, M. Hikita, T. Hosoda, A. Ohta, *Heterocycles*, 1991, 32, 5, 937-947.
37. B. Travis, M. Sivakumar, G. O. Hollist, B. Borhan, *Org. Lett*, 2003, 5, 1031-1034.
38. M. Adamczyk, et al., *Syntetic Comm*, 2002, 32, 20, 3199-3205.
39. Cho G. Y.; Okamura H.; Bolm C. *J. Org. Chem.*, 2005, 70, 2346-2349.
40. P. Molinari, I. Casella, T. Costa; *Biochem J.*, 2008, 409, 251-261.

The invention claimed is:

1. A compound of formula I:

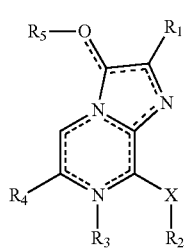

wherein:
$R_1$ is a methyl, benzyl, 4-hydroxy-benzyl, 4-fluoro-benzyl, 4-iodio-benzyl or β-naphthylmethyl group;
$R_2$ is a methyl, phenyl, cyclopentyl, 2-propynyl, 4-fluoro-phenyl, 4-chloro-phenyl, 3-chloro-phenyl, 4-iodio-phenyl, 4-methyl-phenyl, 4-methoxy-phenyl, 4-hydroxy-phenyl, 3,5-bis-trifluoromethyl-phenyl, adamantyl, mercaptobenzyl, an Electron Withdrawing Group (EWG) or an Electron Donating Group (EDG);
$R_3$ is H or 0;
$R_4$ is a H, phenyl, 4-hydroxy-phenyl, 4-amino-phenyl, 4-methoxy-phenyl, 3-pyridinyl, 3,4-(methylendioxy)-phenyl, 2-methoxypyrimidin-5-yl, 4-acetoxy-phenyl or 4-(2,6 diaminohexanoyloxy)-phenyl;
$R_5$ is acetate, pivalate, pivaloyloxymethyl group or 0;
X is oxygen, sulfur, sulfoxide, nitrogen, selenium, iron, copper, cadmium or europium.

2. The compound according to claim 1 wherein $R_3$ is H and $R_5$ is 0.

3. The compound according to claim 2 wherein $R_2$ is a phenyl, cyclopentyl, 2-propynyl, 4-fluoro-phenyl, 4-chloro-phenyl, 4-methyl-phenyl, 4-methoxy-phenyl, 4-hydroxy-phenyl, or adamantyl.

4. The compound according to claim 1 having formula II:

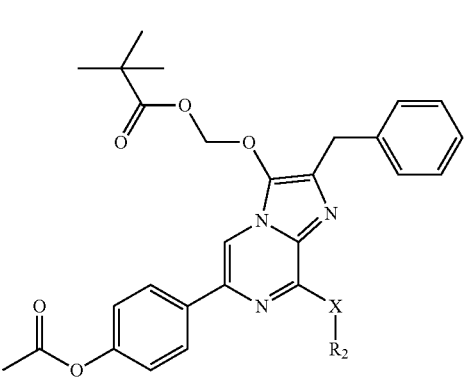

wherein:
$R_2$ is a methyl, phenyl, cyclopentyl, 2-propynyl, 4-fluoro-phenyl, 4-chloro-phenyl, 3-chloro-phenyl, 4-iodio-phenyl, 4-methyl-phenyl, 4-methoxy-phenyl, 4-hydroxy-phenyl, 3,5-bis-trifluoromethyl-phenyl, adamantyl, mercaptobenzyl, an Electron Withdrawing Group (EWG) or an Electron Donating Group (EDG).

5. The compound according to claim 1 having formula III:

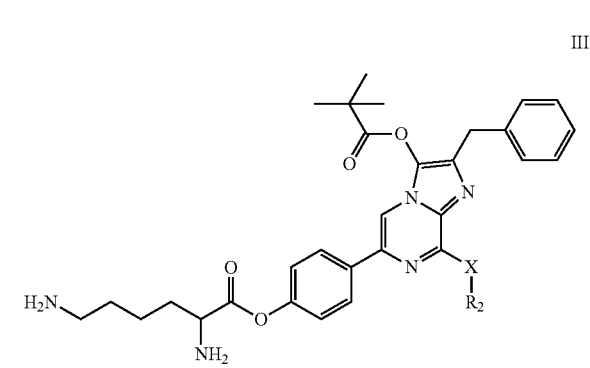

wherein:
$R_2$ is a methyl, phenyl, cyclopentyl, 2-propynyl, 4-fluoro-phenyl, 4-chloro-phenyl, 3-chloro-phenyl, 4-iodio-phenyl, 4-methyl-phenyl, 4-methoxy-phenyl, 4-hydroxy-phenyl, 3,5-bis-trifluoromethyl-phenyl, adamantyl, mercaptobenzyl, an Electron Withdrawing Group (EWG) or an Electron Donating Group (EDG).

6. The compound according to claim 1 wherein X is selenium or cadmium.

7. A compound according to claim 1 selected from the group consisting of:
2-Benzyl-6-phenyl-8-(phenylthio)imidazo-[1,2-a]pirazin-3(7H)-one;

2-Benzyl-6-(4-hydroxyphenyl)-8-(phenylthio)imidazo[1,2-a]pyrazin-3(7H)-one;
2-Benzyl-8-(4-chlorophenylthio)-6-(4-hydroxyphenyl)imidazo[1,2-a]pyrazin-3(7H)-one;
2-Benzyl-6-(4-hydroxyphenyl)-8-(p-tolylthio)imidazo[1,2-a]pyrazin-3(7H)-one;
2-Benzyl-6-phenyl-8-(p-tolylthio)imidazo[1,2-a]pyrazin-3(7H)-one;
2-Benzyl-8-(4-methoxyphenylthio)-6-phenylimidazo[1,2-a]pyrazin-3(7H)-one;
2-Benzyl-8-(4-hydroxyphenylthio)-6-phenylimidazo[1,2-a]pyrazin-3(7H)-one;
2-Benzyl-8-(4-chlorophenylthio)-6-phenylimidazo[1,2-a]pyrazin-3(7H)-one;
2-Benzyl-6-phenyl-8-(4-fluorophenylthio)imidazo-[1,2-a]pirazin-3(7H)-one;
2-Benzyl-6-phenyl-8-(ciclopentylthio)imidazo-[1,2-a]pirazin-3(7H)-one;
2-Benzyl-6-phenyl-8-(adamantylthio)imidazo-[1,2-a]pirazin-3(7H)-one;
2-Benzyl-6-phenyl-8-phenoxyimidazo-[1,2-a]pirazin-3(7H)-one;
2-(4-Hydroxybenzyl)-8-(4-methoxyphenylthio)-6-phenylimidazo[1,2-a]pyrazin-3(7H)-one;
2-(4-Hydroxybenzyl)-8-(cyclopentylthio)-6-phenylimidazo[1,2-a]pyrazin-3(7H)-one;
2-(4-Hydroxybenzyl)-8-phenoxy-6-phenylimidazo[1,2-a]pyrazin-3(7H)-one;
2-Benzyl-6-phenyl-8-(phenylselanyl)imidazo-[1,2-a]pirazin-3(7H)-one;
2-Benzyl-6-(4-hydroxyphenyl)-8-(phenylselanyl)imidazo[1,2-a]pyrazin-3(7H)-one;
2-Benzyl-8-(4-chlorophenylselanyl)-6-(4-hydroxyphenyl)imidazo[1,2-a]pyrazin-3(7H)-one;
2-Benzyl-6-(4-hydroxyphenyl)-8-(p-tolylselanyl)imidazo[1,2-a]pyrazin-3(7H)-one;
2-Benzyl-6-phenyl-8-(p-tolylselanyl)imidazo[1,2-a]pyrazin-3(7H)-one;
2-Benzyl-8-(4-methoxyphenylselanyl)-6-phenylimidazo[1,2-a]pyrazin-3(7H)-one;
2-Benzyl-8-(4-hydroxyphenylselanyl)-6-phenylimidazo[1,2-a]pyrazin-3(7H)-one;
2-Benzyl-8-(4-chlorophenylselanyl)-6-phenylimidazo[1,2-a]pyrazin-3(7H)-one;
2-Benzyl-6-phenyl-8-(4-fluorophenylselanyl)imidazo-[1,2-a]pirazin-3(7H)-one;
2-Benzyl-6-phenyl-8-(ciclopentylselanyl)imidazo-[1,2-a]pirazin-3(7H)-one;
2-Benzyl-6-phenyl-8-(adamantylselanyl)imidazo-[1,2-a]pirazin-3(7H)-one;
2-(4-Hydroxybenzyl)-8-(4-methoxyphenylselanyl)-6-phenylimidazo[1,2-a]pyrazin-3(7H)-one;
2-(4-Hydroxybenzyl)-8-(cyclopentylselanyl)-6-phenylimidazo[1,2-a]pyrazin-3(7H)-one;
(2-Benzyl-3-oxo-6-phenyl-3,7-dihydroimidazo[1,2-a]pyrazin-8-yl)(phenyl)cadmium;
(2-Benzyl-6-(4-hydroxyphenyl)-3-oxo-3,7-dihydroimidazo[1,2-a]pyrazin-8-yl)(phenyl)cadmium;
(2-Benzyl-6-(4-hydroxyphenyl)-3-oxo-3,7-dihydroimidazo[1,2-a]pyrazin-8-yl)(4-chlorophenyl)cadmium;
(2-Benzyl-6-(4-hydroxyphenyl)-3-oxo-3,7-dihydroimidazo[1,2-a]pyrazin-8-yl)(p-tolyl)cadmium;
(2-Benzyl-3-oxo-6-phenyl-3,7-dihydroimidazo[1,2-a]pyrazin-8-yl)(p-tolyl)cadmium;
(2-Benzyl-3-oxo-6-phenyl-3,7-dihydroimidazo[1,2-a]pyrazin-8-yl)(4-methoxyphenyl)cadmium;
(2-Benzyl-3-oxo-6-phenyl-3,7-dihydroimidazo[1,2-a]pyrazin-8-yl)(4-hydroxyphenyl)cadmium;
(2-Benzyl-3-oxo-6-phenyl-3,7-dihydroimidazo[1,2-a]pyrazin-8-yl)(4-chlorophenyl)cadmium;
(2-Benzyl-3-oxo-6-phenyl-3,7-dihydroimidazo[1,2-a]pyrazin-8-yl)(4-fluorophenyl)cadmium;
(2-Benzyl-3-oxo-6-phenyl-3,7-dihydroimidazo[1,2-a]pyrazin-8-yl)(cyclopentyl)cadmium or (2-(4-Hydroxybenzyl)-3-oxo-6-phenyl-3,7-dihydroimidazo[1,2-a]pyrazin-8-yl)(phenyl)cadmium.

8. A composition comprising a compound represented by the compound of formula I according to claim 1 and excipients or diluent or carriers.

9. A chemiluminescent and/or bioluminescent assay method comprising the step of exposing a sample to a compound of represented by the compound of formula I of claim 1, and detecting chemiluminescence and/or bioluminescence.

10. The assay according to claim 9 being an Enzyme-Linked ImmunoSorbent Assay.

11. A kit for performing a chemiluminescent and/or bioluminescent assay comprising a compound represented by the compound of formula I of claim 1.

12. A chemiluminescent and/or bioluminescent assay method comprising the step of exposing a sample to the composition according to claim 8, and detecting chemiluminescence and/or bioluminescence.

13. A kit for performing a chemiluminescent and/or bioluminescent assay comprising the composition according to claim 8.

* * * * *

UNITED STATES PATENT AND TRADEMARK OFFICE
CERTIFICATE OF CORRECTION

| | | |
|---|---|---|
| PATENT NO. | : 8,546,147 B2 | |
| APPLICATION NO. | : 13/383447 | |
| DATED | : October 1, 2013 | |
| INVENTOR(S) | : Germano Giuliani et al. | |

It is certified that error appears in the above-identified patent and that said Letters Patent is hereby corrected as shown below:

In the Claims

Column 42, line 26 in claim 7,
"or" should read -- "and" --.

Column 42, line 34 in claim 9,
"of" should be deleted.

Signed and Sealed this
First Day of April, 2014

Michelle K. Lee
*Deputy Director of the United States Patent and Trademark Office*